US010820803B2

(12) United States Patent
Fukuma et al.

(10) Patent No.: US 10,820,803 B2
(45) Date of Patent: Nov. 3, 2020

(54) PATIENT MANAGEMENT SYSTEM AND PATIENT MANAGEMENT SERVER

(71) Applicant: KABUSHIKI KAISHA TOPCON, Itabashi-ku (JP)

(72) Inventors: Yasufumi Fukuma, Wako (JP); Makoto Fujino, Itabashi-ku (JP); Hisashi Tsukada, Hachioji (JP); Takashi Kubota, Setagaya-ku (JP)

(73) Assignee: KABUSHIKI KAISHA TOPCON, Tokyo (JP)

( * ) Notice: Subject to any disclaimer, the term of this patent is extended or adjusted under 35 U.S.C. 154(b) by 821 days.

(21) Appl. No.: 14/909,652

(22) PCT Filed: Jul. 25, 2014

(86) PCT No.: PCT/JP2014/069653
§ 371 (c)(1),
(2) Date: Feb. 2, 2016

(87) PCT Pub. No.: WO2015/019865
PCT Pub. Date: Feb. 12, 2015

(65) Prior Publication Data
US 2016/0183796 A1 Jun. 30, 2016

(30) Foreign Application Priority Data
Aug. 8, 2013 (JP) .................. 2013-165609

(51) Int. Cl.
*A61B 5/00* (2006.01)
*G16H 40/63* (2018.01)
(Continued)

(52) U.S. Cl.
CPC .......... *A61B 5/0015* (2013.01); *A61B 3/0025* (2013.01); *A61B 3/14* (2013.01);
(Continued)

(58) Field of Classification Search
None
See application file for complete search history.

(56) References Cited

U.S. PATENT DOCUMENTS 5,546,943 A * 8/1996 Gould .................... G06F 3/011
600/425
6,377,349 B1 4/2002 Fercher
(Continued)

FOREIGN PATENT DOCUMENTS

JP 11-325849 A 11/1999
JP 2000-116732 A 4/2000
(Continued)

OTHER PUBLICATIONS

T. W. Shen, W. J. Tompkins and Y. H. Hu, "One-lead ECG for identity verification," Proceedings of the Second Joint 24th Annual Conference and the Annual Fall Meeting of the Biomedical Engineering Society] [Engineering in Medicine and Biology, Houston, TX , USA, 2002, pp. 62-63 vol. 1. (Year: 2002).*
(Continued)

*Primary Examiner* — Rachel L. Porter
(74) *Attorney, Agent, or Firm* — Xsensus LLP

(57) ABSTRACT

A patient management system of an embodiment includes a server, a plurality of ophthalmic examination apparatuses assigned to a plurality of patients, and a plurality of computers installed in a plurality of medical institutions. The ophthalmic examination apparatuses and computers are communicable with the server via a communication line. The server manages the account of each patient, and the account of each medical institution. Test data obtained by each of the ophthalmic examination apparatuses is stored in the account of a corresponding patient. The server sends
(Continued)

information stored in the account of a patient to a computer installed in one of the medical institutions assigned in advance to the patient.

12 Claims, 13 Drawing Sheets

(51) Int. Cl.
- *G16H 40/20* (2018.01)
- *A61B 5/1171* (2016.01)
- *A61B 3/14* (2006.01)
- *A61B 3/00* (2006.01)
- *G06F 19/00* (2018.01)
- *A61B 3/107* (2006.01)

(52) U.S. Cl.
CPC .......... *A61B 5/1171* (2016.02); *G06F 19/328* (2013.01); *G16H 40/20* (2018.01); *G16H 40/63* (2018.01); *A61B 3/107* (2013.01)

(56) References Cited

U.S. PATENT DOCUMENTS

| | | | |
|---|---|---|---|
| 9,047,664 B2* | 6/2015 | Pearson Peyton | G06T 7/0016 |
| 9,510,974 B1* | 12/2016 | Peyman | A61B 5/00 |
| 2006/0025670 A1* | 2/2006 | Kim | G16H 80/00 600/407 |
| 2006/0100528 A1 | 5/2006 | Chan et al. | |
| 2009/0244485 A1* | 10/2009 | Walsh | A61B 3/1005 351/221 |
| 2009/0313049 A1* | 12/2009 | Joao | G06F 19/328 705/3 |
| 2011/0153361 A1* | 6/2011 | Hanina | G06Q 10/10 705/3 |
| 2011/0295617 A1* | 12/2011 | Berger | G06Q 10/10 705/3 |
| 2012/0226132 A1 | 9/2012 | Wong et al. | |
| 2013/0088686 A1* | 4/2013 | Graziano | A61B 3/145 351/206 |
| 2013/0201449 A1 | 8/2013 | Walsh et al. | |
| 2014/0058755 A1* | 2/2014 | Macoviak | G06F 19/328 705/3 |
| 2014/0236629 A1* | 8/2014 | Kim | A61G 7/05 705/3 |
| 2015/0138503 A1 | 5/2015 | Walsh et al. | |

FOREIGN PATENT DOCUMENTS

| | | | |
|---|---|---|---|
| JP | 2002-123613 A | 4/2002 |
| JP | 2002-238858 A | 8/2002 |
| JP | 2004-199631 A | 7/2004 |
| JP | 2005-285033 A | 10/2005 |
| JP | 2006-153838 A | 6/2006 |
| JP | 2006-158592 A | 6/2006 |
| JP | 2007-24677 A | 2/2007 |
| JP | 2007-215694 A | 8/2007 |
| JP | 2008-73099 A | 4/2008 |
| JP | 2008-210328 A | 9/2008 |
| JP | 2009-20794 A | 1/2009 |
| JP | 2011-515194 A | 5/2011 |
| JP | 2013-505078 A | 2/2013 |
| JP | 2013-135976 A | 7/2013 |

OTHER PUBLICATIONS

Farzin, H., Abrishami-Moghaddam, H. & Moin, M. A Novel Retinal Identification System. EURASIP J. Adv. Signal Process. 2008 (Year: 2008).*

Extended European Search Report dated Feb. 14, 2017 in Patent Application No. 14833878.3.

Hadi Farzin, et al., "A Novel Retinal Identification System" EURASIP Journal on Advances in Signal Processing, vol. 2008, No. 1, XP055339566, Apr. 9, 2008, 10 Pages.

International Search Report dated Oct. 7, 2014, in PCT/JP2014/069653 filed Jul. 25, 2014.

Japanese Office Action dated Mar. 6, 2018 in Patent Application No. 2013-165609 (with English translation), 6 pages.

Japanese Office Action dated Sep. 26, 2017 in Patent Application No. 2013-165609.

Japanese Office Action dated Dec. 20, 2018, issued in Japanese Application No. 2018-086671.

* cited by examiner

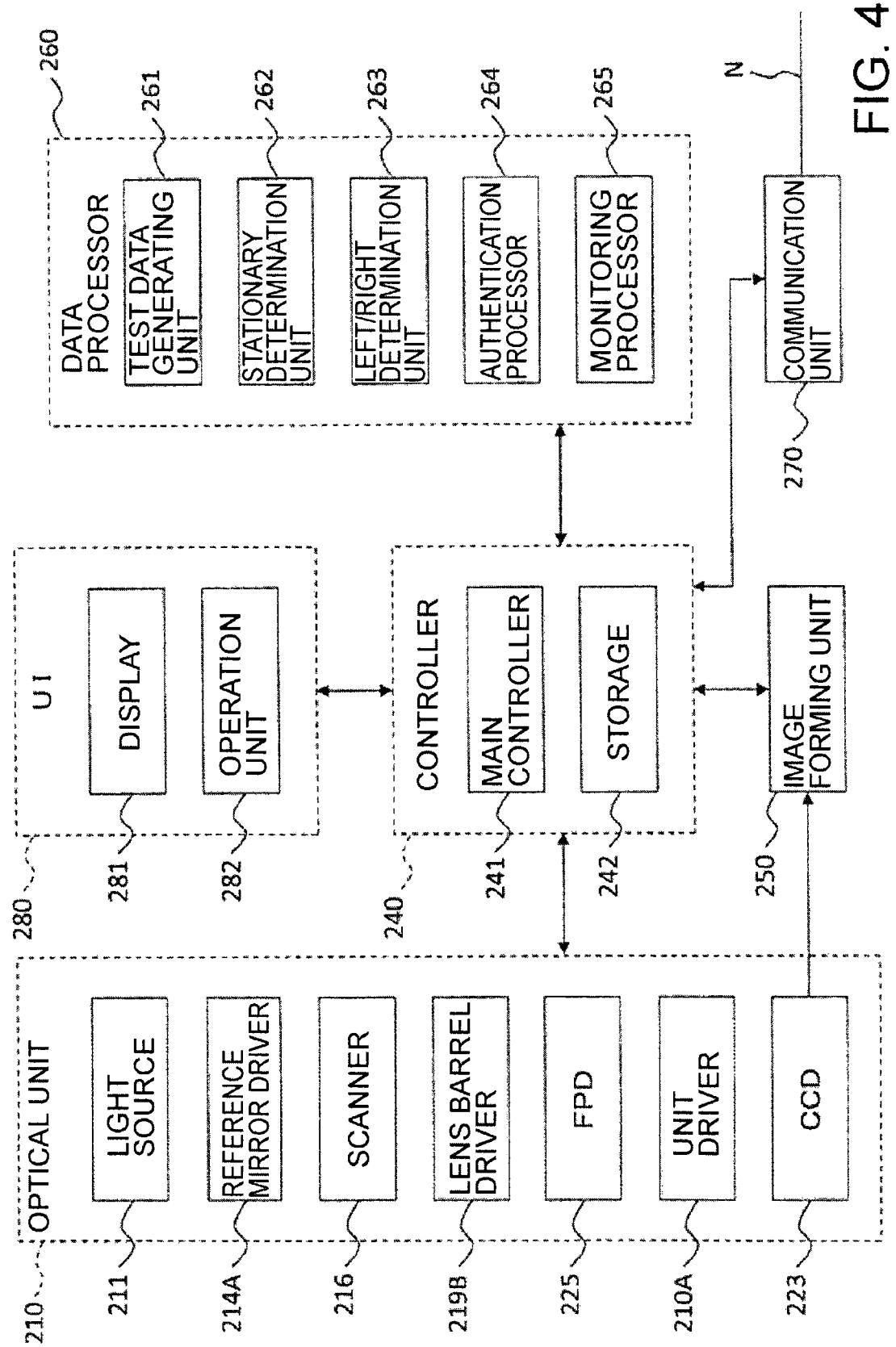

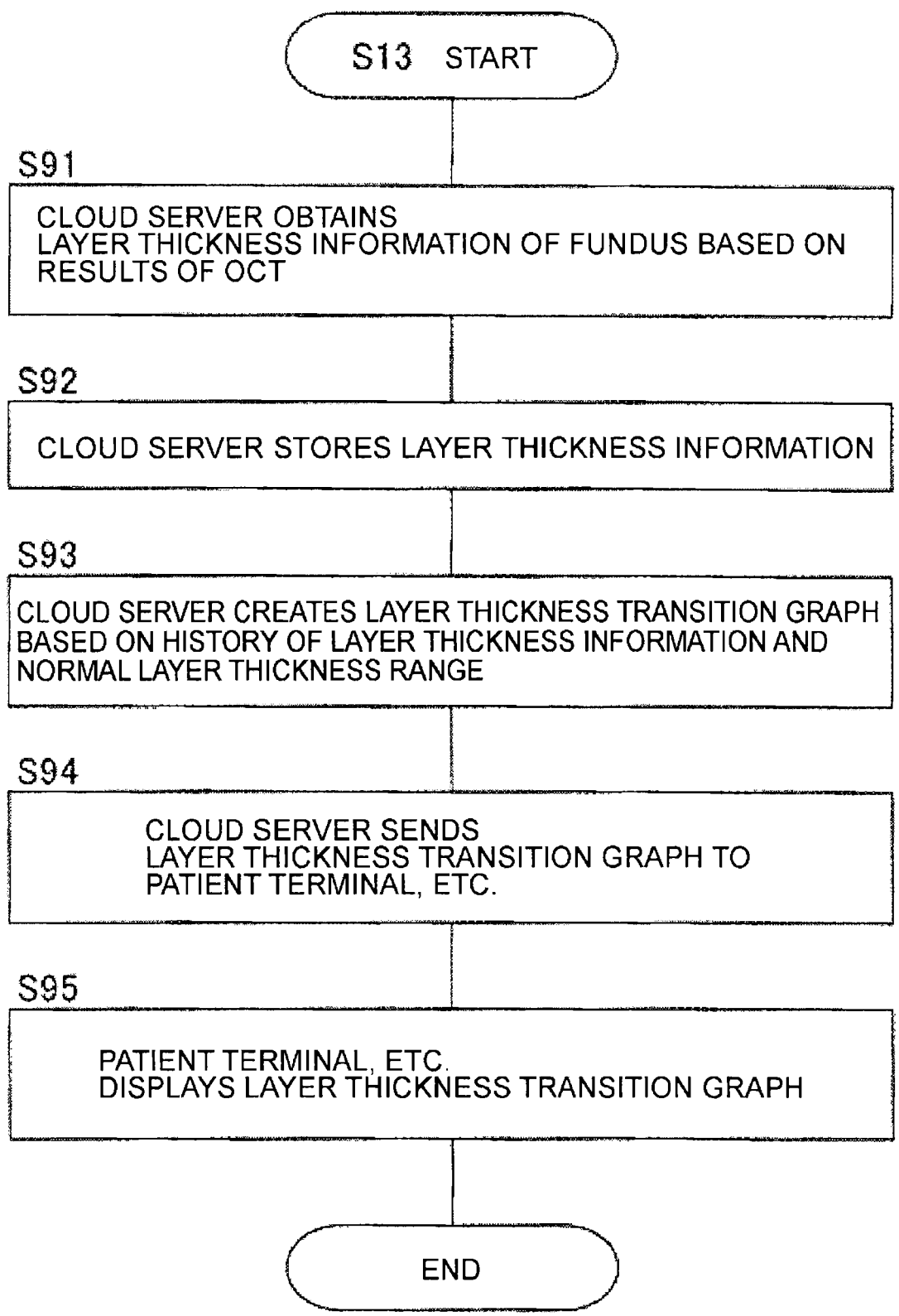

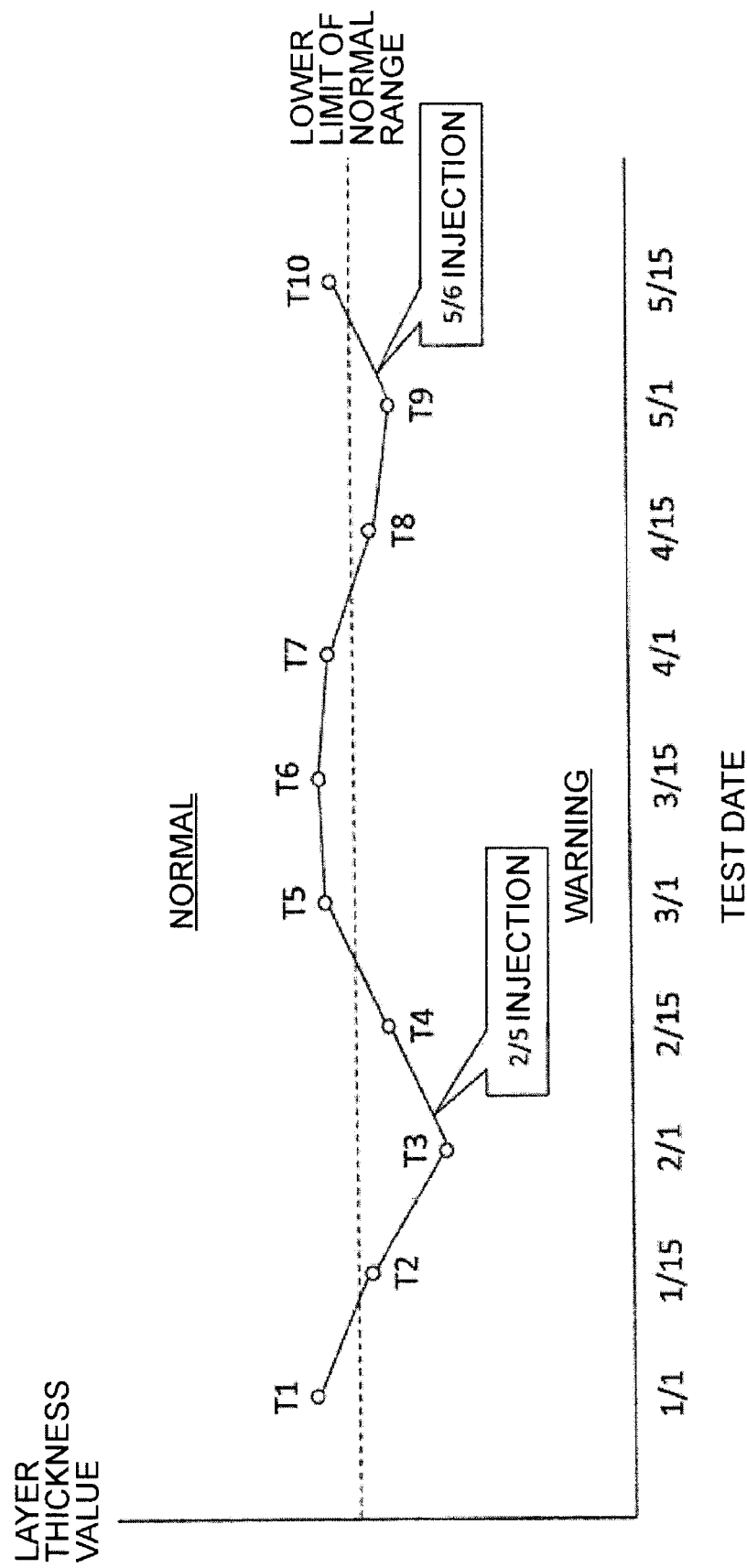

PATIENT MANAGEMENT SYSTEM AND PATIENT MANAGEMENT SERVER

TECHNICAL FIELD

Embodiments described herein relate generally to a system and a server for managing pathological conditions of patients.

BACKGROUND ART

Home care is a service for patients in need of long-term care. Home care is provided to patients in a location other than medical institutions (e.g., home, elderly welfare facilities, etc. collectively referred to as "home"). In a home care, a medical device is installed in a home or the like, and the medical device is remotely managed (see, for example, patent documents 1 to 3).

With the progress of recent aging society, home care is expected to be more common. It is also expected that factors such as aging and changes in the lifestyle cause an increase in ophthalmic diseases including age-related macular degeneration, diabetic retinopathy, glaucoma, and the like. These ophthalmic diseases may lead to blindness, and requires long-term management.

However, it is difficult to manage such ophthalmic disease by conventional home care technology. More specifically, the management of the ophthalmic disease requires understanding the pathological conditions. To accurately understand the pathological conditions, in addition to a subjective test using a visual target, another test has to be performed to figure out the form and properties of the eye.

Examples of devices used to figure out the form of the eye include the following:

Optical coherence tomography (OCT) apparatus for capturing sectional images of the fundus and the cornea using OCT Fundus camera for capturing images of the fundus Scanning laser ophthalmoscope (SLO) for capturing images of the fundus by laser scanning using a confocal optical system Besides, examples of devices used to figure out the properties of the eye include the following:

Eye refraction test device for measuring the refractive properties of the eye (refractometer, keratometer)

Tonometer for measuring the intraocular pressure

Specular microscope for obtaining the properties of the cornea (corneal thickness, cell distribution, etc.)

Wavefront analyzer for acquiring information on the aberration of the eye using a Hartmann-Shack sensor In this way, a variety of test devices are used in the ophthalmic field. Especially, the OCT device is increasingly attracting attention in recent years. This is because the remarkable advantage of the OCT device that it is capable of capturing high-resolution images as well as sectional images and three-dimensional images. As described below, there are various kinds of OCT systems.

Patent Document 4 discloses a device using Fourier-domain OCT or frequency-domain OCT. This device scans an object to be measured with a beam of low-coherence light, and superimposes the light reflected from the object on reference light to generate interference light. The device then obtains the spectral intensity distribution of the interference light by using a spectrometer, and applies Fourier transform to the spectral intensity distribution to acquire an image of a scanned cross-section. Such technique using a spectrometer is called "spectral-domain".

Patent Document 5 discloses a device using swept-source OCT which is another kind of Fourier-domain OCT. This device scans (sweeps) the wavelengths of light irradiated to the object to be measured, and sequentially detects interference light obtained by superimposing reflected light of each wavelength on reference light to acquire spectral intensity distribution. The device applies Fourier transform to the spectral intensity distribution to form an image.

Patent Document 6 discloses a device using full-field OCT or en-face OCT. This device irradiates light beams having a predetermined diameter to an object to be measured, and analyzes the components of interference light obtained by superimposing the reflected light on reference light. Thereby, the device captures an image of a cross-section perpendicular to the traveling direction of the light.

Patent Document 7 discloses a configuration in which OCT is applied to the ophthalmic field. Patent Document 8 discloses an ophthalmic examination apparatus obtained by combining an OCT device and a subjective visual acuity test system, for providing diagnostic material for the maculopathy and the glaucoma.

PRIOR ART DOCUMENTS

Patent Documents

[Patent Document 1] Japanese Unexamined Patent Application Publication No. 2009-20794
[Patent Document 2] Japanese Unexamined Patent Application Publication No. 2005-285033
[Patent Document 3] Japanese Unexamined Patent Application Publication No. 2004-199631
[Patent Document 4] Japanese Unexamined Patent Application Publication No. Hei 11-325849
[Patent Document 5] Japanese Unexamined Patent Application Publication No. 2007-24677
[Patent Document 6] Japanese Unexamined Patent Application Publication No. 2006-153838
[Patent Document 7] Japanese Unexamined Patent Application Publication No. 2008-73099
[Patent Document 8] Japanese Unexamined Patent Application Publication (Translation of PCT Application) No. 2011-515194

SUMMARY OF THE INVENTION

Problems to be Solved by the Invention

An object of the present invention is to provide a technology for managing pathological conditions with an ophthalmic examination apparatus installed in the patient's home or the like.

Means of Solving the Problems

To achieve the object mentioned above, the invention set forth in claim 1 is a patient management system including:
a server;
a plurality of ophthalmic examination apparatuses, which are communicable with the server via a communication line, and are assigned to a plurality of patients; and
a plurality of computers, which are communicable with the server via the communication line, and are installed in a plurality of medical institutions.

Each of the ophthalmic examination apparatuses includes:
a first communication unit configured to communicate with the server via the communication line;

a test unit configured to optically test an eye of a patient who is allowed to use the ophthalmic examination apparatus and generate test data; and a first controller configured to control the first communication unit to send the test data generated by the test unit to the server.

The server includes:

a second communication unit configured to communicate with the ophthalmic examination apparatuses and the computers via the communication line;

an information management unit configured to manage the account of each of the patients, in which the test data is stored, and the account of each of the medical institutions; and a second controller configured to control the second communication unit.

Each of the computers includes:

a third communication unit configured to communicate with the server via the communication line;

a storage; and a third controller configured to, when the third communication unit receives information sent from the second communication unit, store the information in the storage.

The invention set forth in claim 2 is the patient management system of claim 1, further including a first computer terminal, which is communicable with the server via the communication line.

When the second communication unit of the server receives a patient registration request from the first computer terminal, the information management unit creates the account of a patient related to the patient registration request, and assigns one of the medical institutions to the patient, and the second controller controls the second communication unit to send information related to the patient to one of the computers installed in the medical institution assigned to the patient.

The invention set forth in claim 3 is the patient management system of claim 2, wherein, when the second communication unit of the server receives the test data from one of the ophthalmic examination apparatuses, the second controller controls the second communication unit to send the test data to the computer installed in the medical institution assigned to the patient.

The invention set forth in claim 4 is the patient management system of claim 3, wherein the second controller is configured to determine whether to send the test data to the computer, and control the second communication unit to send the test data to the computer only when it has been determined to send the test data.

The invention set forth in claim 5 is the patient management system of claim 2, wherein the server include a test data processor configured to perform predetermined processing on the test data received by the second communication unit from one of the ophthalmic examination apparatuses, and the second controller is configured to control the second communication unit to send a processing result of the test data obtained by the test data processor to the computer installed in the medical institution assigned to the patient.

The invention set forth in claim 6 is the patient management system of claim 5, wherein the second controller is configured to determine whether to send the processing result to the computer, and control the second communication unit to send the processing result to the computer only when it has been determined to send the processing result.

The invention set forth in claim 7 is the patient management system of claim 2, wherein when the second communication unit of the server receives the test data from one of the ophthalmic examination apparatuses, the second controller determines whether to suggest a hospital visit based on the test data received, and when it is determined to suggest a hospital visit, the second controller controls the second communication unit to send a suggestion of a hospital visit to the computer installed in the medical institution assigned to the patient.

The invention set forth in claim 8 is the patient management system of claim 7, further including a second computer terminal, which is communicable with the server via the communication line, and is provided for use by each of the patients or a person related to the patient.

When the second communication unit receives a determination result as to the necessity of a hospital visit from the computer that has received the suggestion of a hospital visit, and if it has been determined that at least a hospital visit is required, the second controller controls the second communication unit to send the determination result to the second computer terminal provided for use by the patient or a person related to the patient.

The invention set forth in claim 9 is the patient management system of claim 1, further including a second computer terminal, which is communicable with the server via the communication line, and is provided for use by each of the patients or a person related to the patient, wherein the server includes a test data analyzer configured to analyze the test data received by the second communication unit from one of the ophthalmic examination apparatus, the second controller is configured to control the second communication unit to send an analysis result of the test data obtained by the test data analyzer to the second computer terminal provided for use by the patient or a person related to the patient.

The invention set forth in claim 10 is the patient management system of claim 1, wherein in the account of each of the patients, morphological information that represents the morphology of the eye of the patient is stored in advance, the test data includes image data that represents the morphology of the eye, the server includes an authentication processor configured to, when the second communication unit receives the test data from one of the ophthalmic examination apparatuses, determine whether the image data represents the morphology of the eye of the patient based on the image data included in the test data and the morphological information stored in the account of the patient, and when the authentication processor determines that the image data represents the morphology of the eye of the patient, the second controller stores the test data in the account of the patient.

The invention set forth in claim 11 is the patient management system of claim 1, further including a second computer terminal, which is communicable with the server via the communication line, and is provided for use by each of the patients or a person related to the patient, wherein the server includes an accounting processor configured to calculate fees to be charged for a paid service when the paid service has been provided to the second computer terminal, and the second controller is configured to store the fees calculated by the accounting processor in the account of the patient, and send information indicating the fees to the second computer terminal provided with the paid service.

The invention set forth in claim 12 is the patient management system of claim 1, wherein the server includes an accounting processor configured to calculate fees to be charged for a paid service when the paid service has been provided to one of the computers, and the second controller is configured to store the fees calculated by the accounting processor in the account of corresponding one of the medical institutions, and send information indicating the fees to the computer provided with the paid service.

The invention set forth in claim 13 is a patient management server configured to be communicable with a plurality of ophthalmic examination apparatuses assigned to a plurality of patients, and a plurality of computers installed in a plurality of medical institutions via a communication line.

The patient management server includes:

a communication unit configured to communicate with the ophthalmic examination apparatuses and the computers via the communication line;

an information management unit configured to manage the account of each of the patients, and the account of each of the medical institutions; and a controller configured to control the communication unit.

The communication unit is configured to receive test data that each of the ophthalmic examination apparatuses has generated by optically testing an eye of a patient.

The information management unit is configured to store the test data in the account of the patient.

The controller is configured to control the communication unit to send information stored in the account of the patient to one of the computers in one of the medical institutions assigned in advance to the patient.

Effects of the Invention

According to the present invention, pathological conditions can be managed with an ophthalmic examination apparatus installed in the patient's home.

BRIEF DESCRIPTION OF THE DRAWINGS

FIG. 4 is a schematic diagram illustrating an example of the configuration of an ophthalmic examination apparatus of one embodiment.

FIG. 7B is a flowchart illustrating an example of the usage of the system of one embodiment.

FIG. 7C is a schematic diagram for explaining an example of the usage of the system of one embodiment.

MODES FOR CARRYING OUT THE INVENTION

Exemplary embodiments of the present invention are described below. Incidentally, the contents of documents cited herein may be incorporated by reference to the following embodiments.

In an embodiment, a cloud server serves a central role in a patient management system. The cloud server provides services to various computers connectable thereto via a communication line.

[System Configuration]

Figure 1:
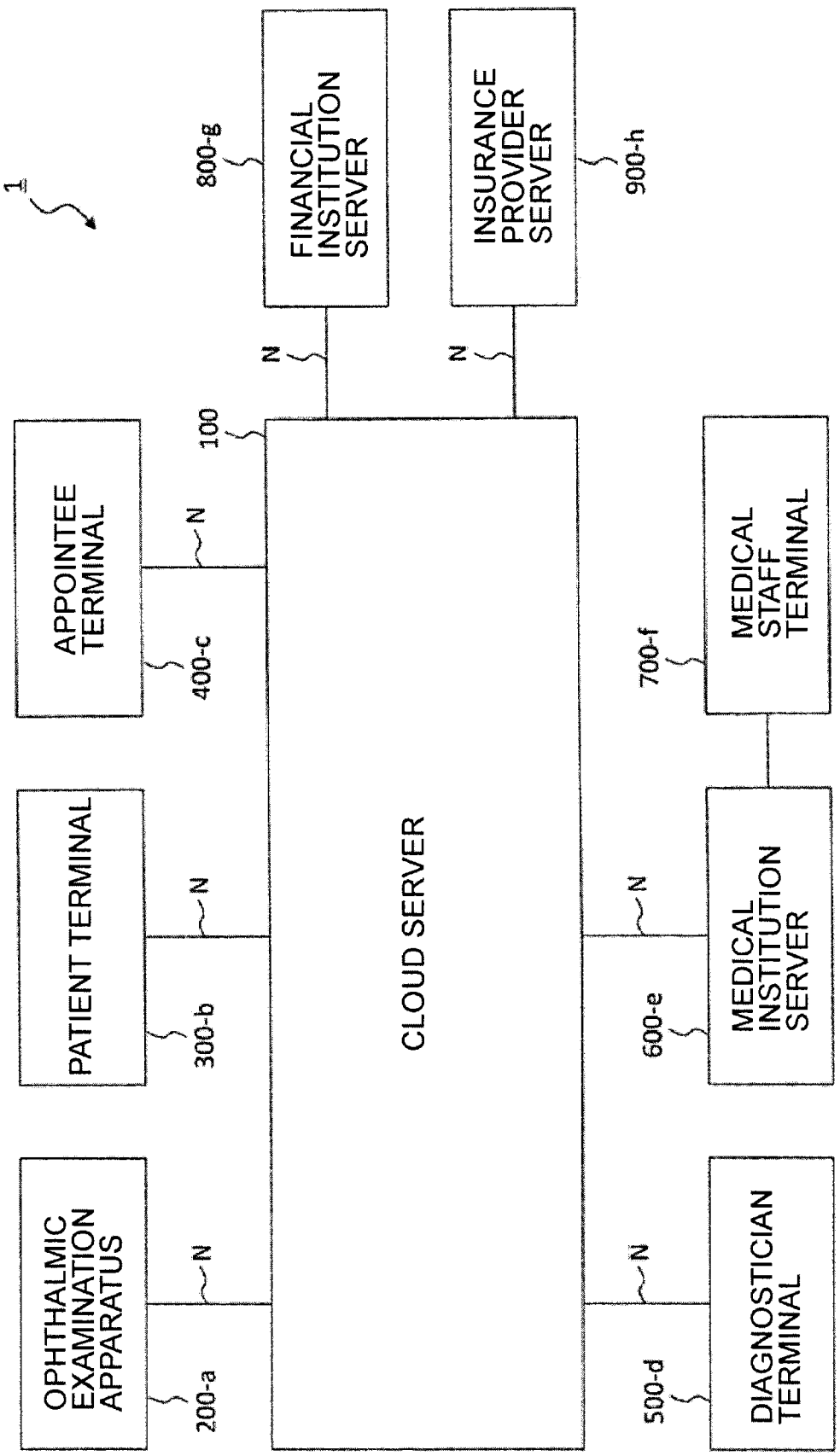
FIG. 1 is a schematic diagram illustrating an example of the configuration of a system according to one embodiment.

As illustrated in FIG. 1, a patient management system 1 includes a cloud server 100, a plurality of ophthalmic examination apparatuses 200-$a$ ($a$=1, 2, 3, . . . ), a plurality of patient terminals 300-$b$ ($b$=1, 2, 3, . . . ), a plurality of appointee terminals 400-$c$ ($c$=1, 2, 3, . . . ), a plurality of diagnostician terminals 500-$d$ ($d$=1, 2, 3, . . . ), a plurality of medical institution servers 600-$e$ ($e$=1, 2, 3, . . . ), a plurality of medical staff terminals 700-$f$ ($f$=1, 2, 3, . . . ), a plurality of financial institution servers 800-$g$ ($g$=1, 2, 3, . . . ), and a plurality of insurance provider servers 900-$h$ ($h$=1, 2, 3, . . . ).

In general, the system of the embodiment need not necessarily include all of these information processing apparatuses. It is sufficient if the system is provided with information processing apparatuses for implementing a predetermined function. Besides, a new information processing apparatus can be added to the system along with the functional enhancement.

These information processing apparatuses are connected via a communication line N. The communication line N includes a wide area network (WAN) such as the Internet, a virtual private network, and a dedicated communication line. The communication line N includes a wired communication network and/or a wireless communication network. Note that the communication line between a medical institution server 600-$e$ and medical staff terminals 700-$f$ that can access this server 600-$e$ may include a local area network (LAN).

[Cloud Server 100]

The cloud server 100 is described below. The cloud server 100 is a server used for so-called cloud computing, and provides services such as data storage and data processing by a computer to a plurality of computers via the communication line N. In this example, the cloud server 100 provides the services to the ophthalmic examination apparatuses 200-$a$, the patient terminals 300-$b$, the appointee terminals 400-$c$, the diagnostician terminals 500-$d$, the medical institution servers 600-$e$, the financial institution servers 800-$g$, and the insurance provider servers 900-$h$.

The cloud server 100 includes a microprocessor, RAM, ROM, a hard disk drive, and the like. The ROM and the hard disk drive store computer programs and data for performing control and arithmetic processing. By the cooperation of hardware such as a microprocessor and software such as the computer programs, various types of processing is performed.

Figure 2:
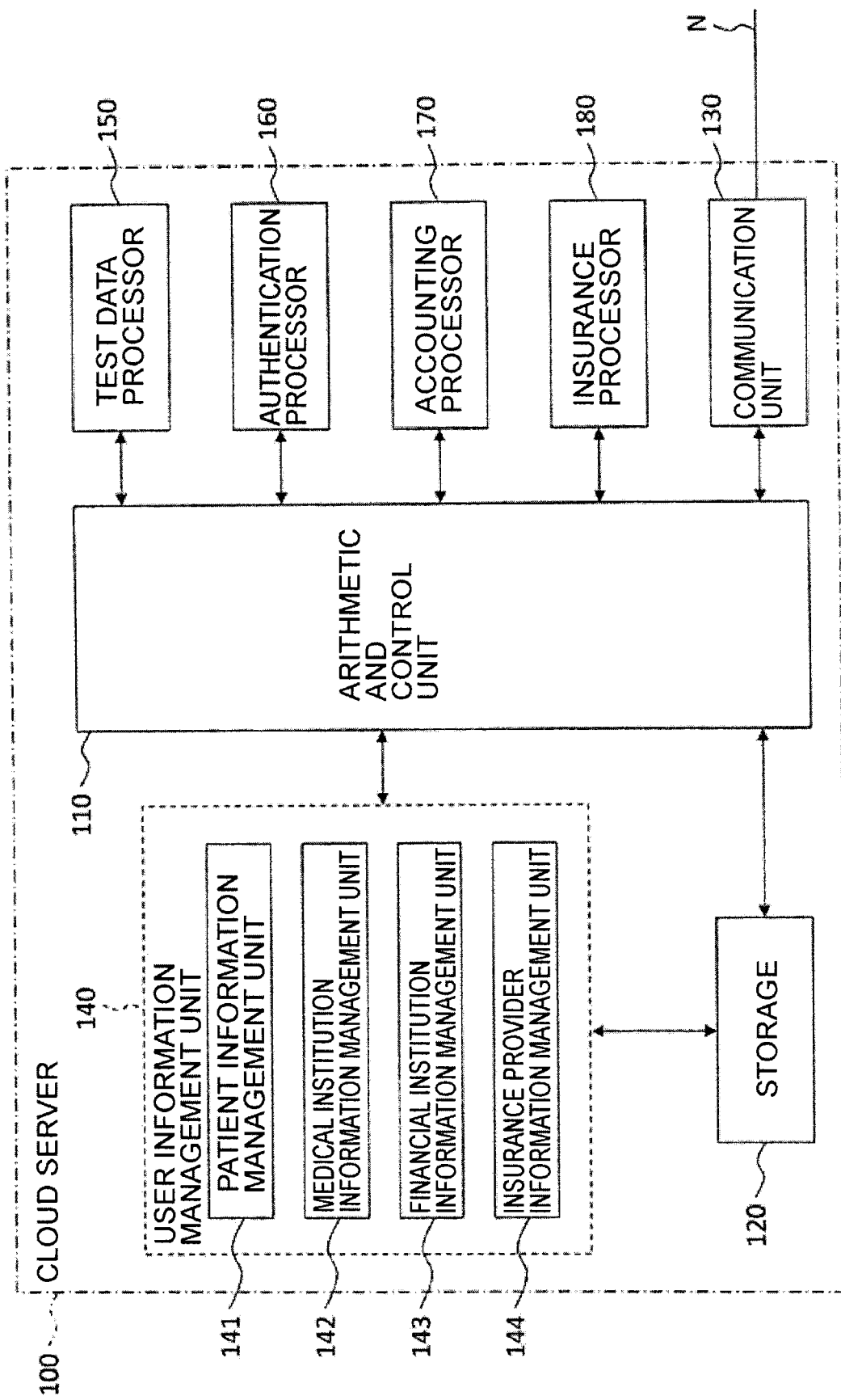
FIG. 2 is a schematic diagram illustrating an example of the configuration of a cloud server of one embodiment.

FIG. 2 illustrates an example of the internal configuration of the cloud server 100. The cloud server 100 of this embodiment includes an arithmetic and control unit 110, a storage 120, a communication unit 130, a user information management unit 140, a test data processor 150, an authentication processor 160, an accounting processor 170, and an insurance processor 180.

(Arithmetic and Control Unit 110)

The arithmetic and control unit 110 controls each unit of the cloud server 100, and performs various types of arithmetic processing. Specific examples of the processing performed by the arithmetic and control unit 110 are described later.

(Storage 120)

The storage 120 stores various types of data. The storage 120 stores information related to the services provided by the cloud server 100. The receivers of the services, i.e., the users of the services include patients, those related to the patients (family members, etc.), medical institutions, financial institutions, insurance providers, and the like. With respect to these users, for example, the following information is stored in the storage 120.

The storage 120 stores information related to a patient as a user. Examples of the information include user ID (identifier) in the service, authentication information (password, etc.), name, sex, date of birth, contact information (address, phone number, e-mail address, IP address, etc.), information about accounting, ID in the relevant medical institution (patient ID), medical information (part of electronic medical record information, information acquired by the ophthalmic examination apparatuses 200-*a*, etc.), user ID or account ID in the relevant financial institution, user ID or insured ID in the related insurance provider, and the like.

Note that the user ID of the patient user is not limited to the identifier assigned to the patient, but may be, for example, an identifier assigned to the ophthalmic examination apparatuses 200-*a* that the patient uses, contact information (IP address, etc.), or the like. The authentication information is not limited to character string information such as a password, but may be, for example, biometric authentication information.

The storage 120 also stores information on a user related to the patient. Examples of the information include user ID in the service, authentication information (password, etc.), name, relationship with the patient, contact information (address, phone number, e-mail address, IP address, etc.), and information about accounting.

The storage 120 also stores information related to a medical institution as a user. Examples of the information include user ID in the service, authentication information (password, etc.), the type of the medical institution (hospital, clinic, medical center, etc.), the name of the medical institution, department, information about the relevant medical personnel (the name of the doctor, disease that he/she specializes in, etc.), contact information (address, phone number, e-mail address, IP address, etc.), a list of relevant medical institutions, user ID or patient ID of the patient involved, and information about accounting.

The storage 120 also stores information related to a financial institution as a user. Examples of the information include user ID in the service, authentication information (password, etc.), the type of the financial institution (bank, credit card company, etc.), the name of the financial institution, contact information (address, phone number, e-mail address, IP address, etc.), user ID or patient ID of the patient involved, and information about accounting.

The storage 120 also stores information related to an insurance provider as a user. Examples of the information include user ID in the service, authentication information (password, etc.), the type of the insurance provider (public insurance, private insurance, etc.), the name of the insurance provider, contact information (address, phone number, e-mail address, IP address, etc.), user ID or insured ID of the patient involved, and information about accounting.

(Communication Unit 130)

The communication unit 130 communicates data with other information processing apparatuses through the communication line N. The data communication may be performed by any method or system. The communication unit 130 includes, for example, a communication interface in accordance with the Internet, a communication interface in accordance with LAN, and a communication interface in accordance with near field communication, and the like. Data that the communication unit 130 transmits and receives may be encrypted. In this case, the arithmetic and control unit 110 includes an encryption processor that encrypts transmission data and a decoder that decodes received data.

(User Information Management Unit 140)

The user information management unit 140 performs processing on information about the users of the service. As described above, the users of the service include patients, those related to patients, medical institutions, financial institutions, insurance providers, and the like. The user information management unit 140 has a function corresponding to the types of users of the service. In this embodiment, the user information management unit 140 is provided with a patient information management unit 141, a medical institution information management unit 142, a financial institution information management unit 143, and an insurance provider information management unit 144.

(Patient Information Management Unit 141)

The patient information management unit 141 manages the account of patient users who use the service. The account is created for each patient, and is identified by, for example, a user ID assigned to the patient user. The patient information management unit 141 manages information about the patient user (as described above), and information about a user related to the patient (as described above). Specific examples of processing performed by the patient information management unit 141 are described later.

(Medical Institution Information Management Unit 142)

The medical institution information management unit 142 manages information about medical institution users who use the service (as described above) by, for example, providing an account for each medical institution. The account is identified by, for example, a user ID assigned to the medical institution user. Specific examples of processing performed by the medical institution information management unit 142 are described later.

(Financial Institution Information Management Unit 143)

The financial institution information management unit 143 manages information about financial institution users who use the service (as described above) by, for example, providing an account for each financial institution. The account is identified by, for example, a user ID assigned to the financial institution user. Specific examples of processing performed by the financial institution information management unit 143 are described later.

(Insurance Provider Information Management Unit 144)

The insurance provider information management unit 144 manages information about insurance provider users who use the service (as described above) by, for example, providing an account for each insurance provider. The account is identified by, for example, a user ID assigned to the insurance provider user. Specific examples of processing performed by the insurance provider information management unit 144 are described later.

The cloud server 100 may have a function (apparatus management unit) for managing the status of each of the ophthalmic examination apparatuses 200-a. The apparatus management unit stores identification information of each of the ophthalmic examination apparatuses 200-a and status information in association with each other. The status information indicates the operating state of each ophthalmic examination apparatus 200-a (e.g., a state of being lent to a patient user, a state of waiting to be lent, during maintenance, etc.). If an ophthalmic examination apparatus 200-a is being lent, the status information thereof may include the user ID of a patient user that borrows the apparatus and the like. In addition, when an ophthalmic examination apparatus 200-a is currently undergoing maintenance, the status information thereof may include maintenance schedule and the like.

(Test Data Processor 150)

Figure 3:
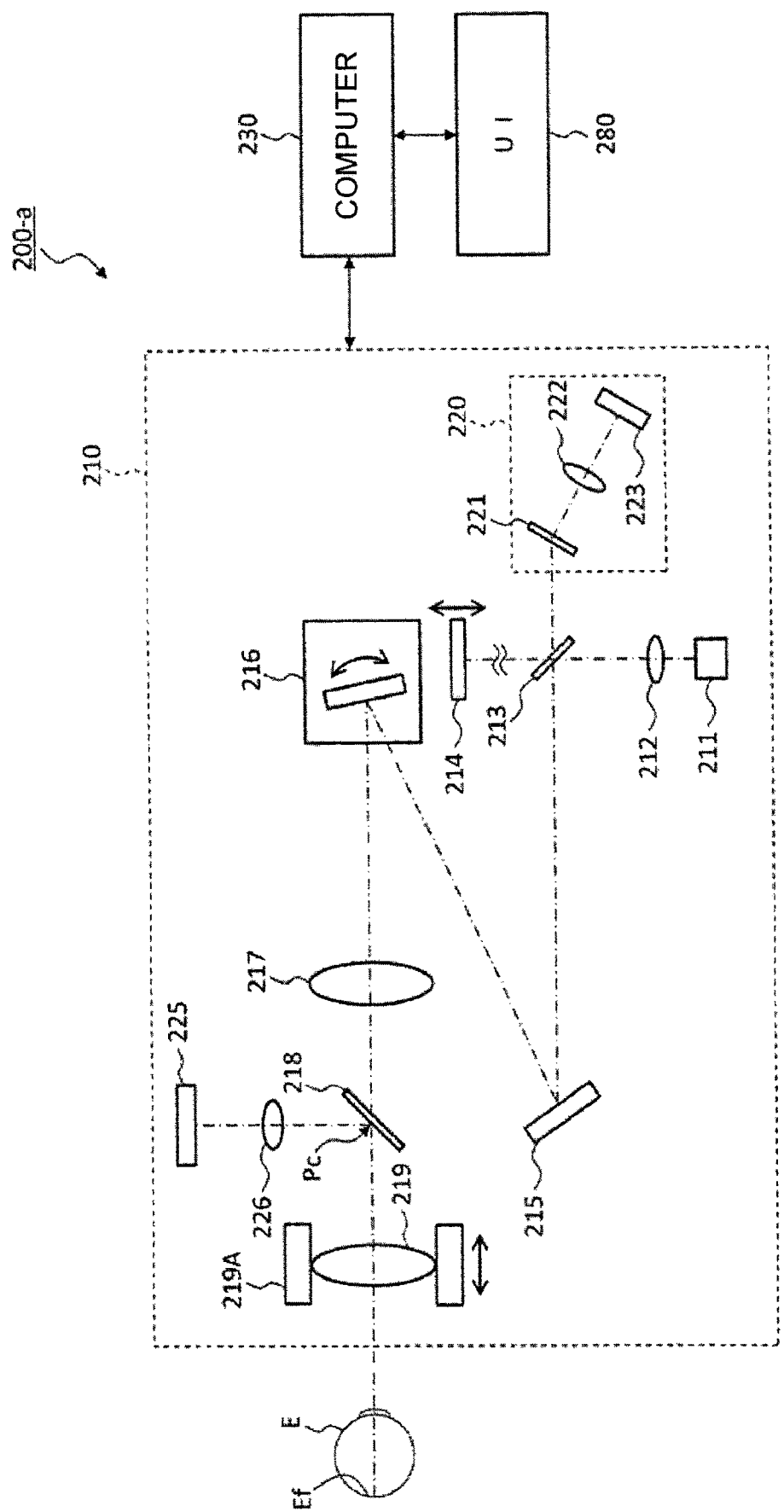
FIG. 3 is a schematic diagram illustrating an example of the configuration of an ophthalmic examination apparatus of one embodiment.

The test data processor 150 performs processing on data (test data) received from the ophthalmic examination apparatuses 200-a. Examples of the test data includes the following:

(1) signals output from a CCD image sensor 223 illustrated in FIG. 3 and the like;

(2) image data generated by an image forming unit 250 illustrated in FIG. 4;

(3) data obtained in the middle of processing of the image forming unit 250 (i.e., data obtained in the middle of an image data forming process); and (4) data obtained by processing signals output from the CCD image sensor 223 by a component other than the image forming unit 250.

When an ophthalmic examination apparatus 200-a have a function of forming image data, i.e., when the ophthalmic examination apparatus 200-a include the image forming unit 250, for example, any of the above test data (1) to (4) is input to the cloud server 100. Meanwhile, when the ophthalmic examination apparatus 200-a does not have a function of forming image data, for example, the above test data (1) and/or (4) is input to the cloud server 100. In this case, the test data processor 150 has the same function as the image forming unit 250. Besides, when the ophthalmic examination apparatuses 200-a have a function of processing image data generated by the image forming unit 250, the test data (4) may be obtained by this function. Examples of this function include fundus layer thickness analysis, drusen analysis, optic disc shape analysis (described later), and the like.

Although the test data described above are obtained by OCT, the test data may be data obtained by other tests. Examples of the other tests include subjective visual acuity test (described later).

Described below are examples of processing performed by the test data processor 150. As a first example, the test data processor 150 may generate layer thickness information of the fundus based on test data obtained by OCT. In other words, the test data processor 150 can perform the fundus layer thickness analysis (retinal thickness analysis, RNFL thickness analysis, etc.). Further, the test data processor 150 is capable of performing comparative analysis between the layer thickness information obtained by the fundus layer thickness analysis and standard layer thickness values (e.g., standard layer thickness values regarding a healthy eye).

The fundus layer thickness analysis is a process of obtaining the thickness (distribution thereof) of a predetermined layer tissue of the fundus based on the test data obtained by OCT. As an example, the retinal thickness analysis is explained. Similar process can be performed upon determining the thickness of another layer tissue.

In the retinal thickness analysis, for example, a cross-sectional image or a three-dimensional image of the fundus is analyzed to obtain the thickness distribution of the retina in part or all of the scan area by OCT. Note that the retinal thickness has a variety of definitions. For example, the retinal thickness may be defined as a thickness from the inner limiting membrane to the inner nuclear layer (photoreceptor inner segment/outer segment (IS/OS) junction), or a thickness from the inner limiting membrane to the retinal pigment epithelium. The retinal thickness obtained by the retinal thickness analysis may be calculated according to one of such definitions.

For example, the retinal thickness analysis is performed in the following manner. First, an OCT image of the fundus is analyzed to specify an image area corresponding to predetermined boundary sites (e.g., the inner limiting membrane and the retinal pigment epithelium). Then, the number of pixels between specified boundary sites is counted to obtain the retinal thickness (distance in the depth direction). For the process of analyzing an OCT image to obtain the thickness of the fundus layer, reference may be had to, for example, Japanese Unexamined Patent Application Publication Nos. 2007-325831, 2008-206684, 2009-61203, and 2009-66015 filed by the present applicant.

The comparative analysis of the retinal thickness is an analysis comparing the retinal thickness obtained by the retinal thickness analysis and normative data stored in advance. The normative data indicates standard thickness values of the retinas of healthy eyes. The normative data is created by measuring the retinal thickness of a number of healthy eyes, and calculating statistical values of the measurement results (average values, standard deviations, etc.). The comparative analysis determines whether the retinal thickness of the subject's eye E is within the range of that of healthy eyes. Incidentally, when the range of the retinal thickness values of diseased eyes is referred to, the comparative analysis may be performed by determining whether the retinal thickness obtained by the retinal thickness analysis is within this range.

The test data processor 150 may be configured to be capable of performing the drusen analysis. The drusen analysis is a process of analyzing, for example, an OCT image to obtain the distribution of drusen in part or all of the scan area. The distribution may include the positions and sizes (areas, volumes, diameters) of the drusen in the eye fundus, and the like.

In the drusen analysis, for example, an OCT image is analyzed to specify an image area corresponding to the Bruch's membrane and an image area corresponding to the retinal pigment epithelium. Then, image areas corresponding to small substantially circular raised shapes are specified as drusen (candidates thereof) based on pixel values between the image areas corresponding to the Bruch's membrane and the retinal pigment epithelium. The process of specifying the image area based on such a shape can be carried out by, for example, image matching with a template of the shape. Further, the test data processor 150 obtains the positions, numbers, sizes, and the like of drusen based on the image areas corresponding to the drusen thus specified. Further, evaluation information can be generated for the state of age-related macular degeneration based on the distribution of the drusen acquired.

Incidentally, when the test data includes a front image of the fundus, the drusen analysis can be performed based on the front image. In this drusen analysis, for example, it is determined whether the pixel value of each pixel in the front image falls within a predetermined range to specify pixels in the range. If the front image is a color image, drusen are represented in a specific color (yellowish white). Accordingly, a range of pixel values corresponding to the specific color is set as the predetermined range in advance. Besides, if the front image is a monochrome image, drusen are represented with characteristic brightness (luminance). Accordingly, a range of pixel values corresponding to the characteristic brightness is set as the predetermined range in advance. Further, image areas corresponding to drusen can be specified by performing template matching based on the standard form of drusen (small substantially circular raised shape) or the like.

The optic disc shape analysis may include a process in which a cross-sectional image or a three-dimensional image of the fundus is analyzed to detect a hole (cut, defect site) in the retina, and thereby determining the shape of the optic disc. In the optic disc shape analysis, for example, a cross-sectional image or the like is analyzed to specify an image area corresponding to the optic disc and the retinal surface near it. The image area thus specified is analyzed to obtain a parameter (optic disc shape parameter) representing the global shape and/or the local shape (concavity and convexity). Examples of the optic disc shape parameter include the cup diameter, the disc diameter, and the rim diameter of the optic disc as well as the depth of the optic disc, and the like.

In addition, the optic disc shape analysis may include a process of obtaining a tilt of the optic disc (asymmetry of the shape). For example, this analysis process is performed in the following manner. First, the test data processor 150 analyzes a three-dimensional image obtained by scanning an area including the optic disc to specify the center of the optic disc. Next, the test data processor 150 sets a circular area around the center of the optic disc, and divides the circular area radially to obtain a plurality of partial areas. Subsequently, the test data processor 150 analyzes a cross-sectional image of the circular area to obtain the height position of a predetermined layer (e.g., the retinal pigment epithelium layer) at each pixel location. Further, the test data processor 150 calculates the average values of height positions of the predetermined layer in the respective partial areas. Next, the test data processor 150 compares a pair of average values obtained for a pair of partial areas corresponding to opposite positions with respect to the center of the optic disc to obtain a tilt of the fundus in the opposite directions. The test data processor 150 generates tilt distribution information indicating the distribution of the tilts of the fundus in the circular area based on the tilts obtained for a plurality of opposite directions. In addition, evaluation information can be generated for the state of disease based on the tilt distribution information thus generated (and information indicating the standard distribution thereof).

(Authentication Processor 160)

The authentication processor 160 performs user authentication. As described above, each user of the service is assigned a user ID. In response to a request for the use of the service from an external information processing apparatus, the authentication processor 160 determines whether to accept the request.

Described below is an example of the authentication process. As described above, the storage 120 stores the user ID of each user and authentication information for the authorized users (authorized user authentication information). It is assumed that the request received from the external information processing apparatus includes a user ID (or similar character string information, etc.) and user authentication information (or similar character string information, etc.). Upon receipt of the request, the authentication processor 160 checks a combination of the user ID and the user authentication information included in the request with combinations of user ID and authorized user authentication information stored in the storage 120. That is, the authentication processor 160 searches the storage 120 for a combination of a user ID and authorized user authentication information that matches the combination of the user ID and the user authentication information included in the request. Having found the combination matched, the authentication processor 160 determines that the person who has sent this request is a registered user of the service. On the other hand, if such a combination is not found, the authentication processor 160 determines that the person who has sent this request is not a registered user of the service. The determination result is sent to the arithmetic and control unit 110. The arithmetic and control unit 110 performs predetermined processing according to the determination result.

There are cases where two or more patient users share one of the ophthalmic examination apparatuses 200-*a*. In other words, there may be two or more authorized patient users for one of the ophthalmic examination apparatuses 200-*a*. In this case, as described above, an identifier assigned to the one of the ophthalmic examination apparatuses 200-*a* may be used as the user ID. In this case, these patient users are assigned the same user ID and different user authentication information. Therefore, to identify the patient users, a combination of the user ID and the user authentication information can always be used. That is, the combination can be used as the user ID. With this configuration, two or more patient users can be authorized individually.

(Accounting Processor 170)

The accounting processor 170 performs processing related to the use fee of the service that the cloud server 100 provides. The use fee is charged to any kinds of users among patient users, users related to the patients, medical institution users, financial institution users, and insurance provider users. Each service that involves a charge may be an option, or it may be a default.

Examples of paid services that the cloud server 100 provides to a patient user include the following:

Management of account by the patient information management unit 141;

Installation of the ophthalmic examination apparatus (200-*a*) in a home, etc. (rental, loan, purchase, etc.);

Test using the ophthalmic examination apparatus (200-*a*);

Processing of test data by the test data processor 150;

Provision of processing results of the test data to the patient user and/or users related to the patient;

Storage of the test data in the account of the patient user;

Provision of maintenance service for the ophthalmic examination apparatus (200-*a*);

Provision of social networking services such as blog function, bulletin board function, and the like;

Provision of services that a financial institution user provides to the patient user on behalf of the financial institution; and Provision of services that an insurance provider user provides to the patient user on behalf of the insurance provider.

Examples of paid services that the cloud server 100 provides to users related to a patient user include the following:

Creation and management of account for the users related to the patient;

Provision of processing results of test data to the users related to the patient;

Provision of social networking services such as blog function, bulletin board function, and the like;

Provision of services that a financial institution user provides to the users related to the patient on behalf of the financial institution; and Provision of services that an insurance provider user provides to the users related to the patient on behalf of the insurance provider.

Examples of paid services that the cloud server 100 provides to a medical institution user include the following:

Management of account by the medical institution information management unit 142;

Introduction of a new patient user to the medical institution user;

Introduction of a patient user who wishes to be transferred to another hospital to the medical institution user;

Contingency fee for the introduction of a patient user;

Provision of statistical information related to a patient user(s)

Access to specific or non-specific patient users (questionnaires, etc.);

Access to other medical institution users (second opinion, referral letter, etc.);

Use of information related to analysis process (normative data, etc.);

Own or use of an ophthalmic examination apparatus (rental, loan, purchase, etc.);

Processing of test data by the test data processor 150;

Provision of processing results of the test data to the medical institution user;

Management of test data for a predetermined patient user by the account of the medical institution user;

Provision of maintenance service for the ophthalmic examination apparatus;

Provision of social networking services such as blog function, bulletin board function, and the like;

Provision of services that a financial institution user provides to the medical institution user on behalf of the financial institution;

Provision of services that an insurance provider user provides to the medical institution user on behalf of the insurance provider;

Provision of advertisement of the medical institution user to patient users and the like; and Contingency fee for the advertisement.

Examples of paid services that the cloud server 100 provides to a financial institution user include the following:

Creation and management of account for the financial institution user;

Provision of information on charges to users (debit amount, etc.);

Provision of social networking services such as blog function, bulletin board function, and the like;

Provision by the cloud server 100 of services that the financial institution user provides on behalf of the financial institution user;

Provision of advertisement of the financial institution user to patient users and the like; and Contingency fee for the advertisement.

Examples of paid services that the cloud server 100 provides to an insurance provider user include the following:

Creation and management of account for the insurance provider user;

Provision of information on the insurance of patient users (history of hospital attendance, payments, etc.);

Provision of information on the insurance of medical institution users (medical remuneration points, receipt, etc.);

Provision of social networking services such as blog function, bulletin board function, and the like;

Provision by the cloud server 100 of services that the insurance provider user provides on behalf of the insurance provider user;

Provision of advertisement of the insurance provider user to patient users and the like; and Contingency fee for the advertisement.

The accounting processor 170 stores in advance a fee for each paid service. This information is, for example, table information associating the types of the paid services with fees to be charged. When a service corresponding to the paid service is provided to a certain user, the arithmetic and control unit 110 sends the user ID of the user and the type information of the service to the accounting processor 170. The accounting processor 170 acquires a fee corresponding to the type information with reference to the table information described above. Then, the accounting processor 170 associates the fee with the user ID, and sends them to the arithmetic and control unit 110. The arithmetic and control unit 110 sends the information received from the accounting processor 170 to the user information management unit 140. The user information management unit 140 stores the amount of the fee in an account identified by the user ID. At this time, information related to the service (provision date and time, type, etc.) can be stored with the amount of the fee.

(Insurance Processor 180)

The insurance processor 180 provides processing related to insurance. Incidentally, the accounting processor 170 can perform processing for paid services related to insurance. The insurance processor 180 performs, for example, processing related to insurance contract already concluded with a certain patient user and a certain insurance provider user. As described above, the storage 120 stores information indicating the relationship between the insurance provider users and the patient users. This information is, for example, table information associating the user IDs of the patient users with the user IDs of the insurance provider users. With reference to such information, the insurance processor 180 can determine an insurance provider that a certain patient user has a contract with and, on the contrary, a patient user that a certain insurance provider has a contract with.

As a specific example, when a patient user receives medical practice in a medical institution, the cloud server 100 retrieves preset information (disease name, medical fee, etc.) from one of the medical institution servers 600-*e* of the medical institution together with the patient user ID. For example, with reference to the table information, the insurance processor 180 specifies an insurance provider user that corresponds to the patient user. The arithmetic and control unit 110 controls the communication unit 130 to send (at least part of) the information retrieved from one of the medical institution servers 600-*e* to the insurance provider user specified by the insurance processor 180.

[Ophthalmic Examination Apparatuses 200-*a*]

Described below is an example of the configuration of the ophthalmic examination apparatuses 200-*a*. The ophthalmic examination apparatuses 200-*a* are used for optical test of the eye. The ophthalmic examination apparatuses 200-*a* each have a function as an ophthalmologic imaging apparatus and/or a function as an ophthalmic measurement apparatus. Examples of the ophthalmic imaging apparatus include optical coherence tomography (OCT device), fundus camera, scanning laser ophthalmoscope, and the like. Examples of the ophthalmic measurement apparatus include eye refraction test device, tonometer, specular microscope, wave front analyzer, and the like. In this embodiment, the application of the OCT device is described in detail; however, a similar embodiment can be applied to any other ophthalmic examination apparatuses.

Incidentally, an image acquired by OCT may be hereinafter referred to as OCT image. In addition, measurement for forming an OCT image may be hereinafter referred to as OCT measurement.

In this embodiment, a description is given of a so-called spectral-domain OCT device including a low-coherence light source and a spectrometer; however, a similar embodiment can be applied to other types of OCT devices such as, for example, swept-source OCT devices. The swept-source OCT is a technique for imaging the morphology of an object to be measured in the following manner. First, the wavelength of light irradiated to the object is scanned (wavelength sweep). Next, interference light obtained by superimposing reference light and reflected light of each wavelength is sequentially detected to obtain spectral intensity distribution. Then, Fourier transform is applied to the spectral intensity distribution.

The ophthalmic examination apparatuses 200-a of the embodiment may have an imaging function other than OCT. As an example of the additional imaging function may be cited a function of capturing a front image of the anterior segment and/or the fundus of the eye. This may be realized by, for example, the same configuration as a conventional fundus camera.

Described below is the configuration of the ophthalmic examination apparatus according to the embodiment. The system of this embodiment includes the ophthalmic examination apparatuses 200-a. FIG. 3 illustrates an example of the configuration of the ophthalmic examination apparatuses 200-a. As illustrated in FIG. 3, the ophthalmic examination apparatuses 200-a each includes an optical unit 210, a computer 230, and a user interface (UI) 280.

(Optical Unit 210)

The optical unit 210 includes an optical system for performing OCT measurement and mechanisms for driving predetermined optical elements. The optical system splits light from a light source 211 into measurement light and reference light, and causes the measurement light returning from the subject's eye E to interfere with the reference light, thereby detecting the interference light. The optical system has the same configuration as a conventional spectral-domain OCT device. That is, the optical system is configured to divide low-coherence light (broad band light) into reference light and measurement light, causes the measurement light having passed through the subject's eye E to interfere with the reference light having propagated through the reference optical path to generate interference light, and detect spectral components of the interference light. The detection result of the spectral components (detection signal) is sent to the computer 230.

If swept-source OCT is used, the low-coherence light source is replaced by a wavelength-swept light source, and an optical member is not provided for spectral decomposition of interference light. Besides, for example, a balanced photodiode is provided as an element for detecting the interference light. In general, a known technology can be arbitrarily applied to the configuration of the optical unit 210 according to the type of OCT.

The light source 211 outputs wide-band low-coherence light. The low-coherence light includes, for example, wavelengths in the near-infrared region (about 800 nm to 900 nm), and has a temporal coherence length of about several tens of micrometers. Incidentally, the low-coherence light may be near infrared light of wavelengths invisible to the human eye, for example, with a center wavelength of about 1040 nm to 1060 nm.

The light source 211 includes a light output device, such as a super luminescent diode (SLD), a light-emitting diode (LED), or a semiconductor optical amplifier (SOA).

The low-coherence light output from the light source 211 is collimated into a parallel light flux by a collimator lens 212 and guided to a beam splitter 213. The beam splitter 213 is, for example, a half mirror that reflects a predetermined proportion of light and transmits the rest. The beam splitter 213 splits the parallel light flux into measurement light and reference light.

The measurement light is light that is irradiated to the subject's eye E (also referred to as signal light or the like). A group of optical elements which forms the optical path of the measurement light (measurement optical path) is referred to as a measurement arm (also referred to as a sample arm or the like). The reference light serves as a reference to extract information included in return light of the measurement light as an interference signal. A group of optical elements which forms the optical path of the reference light (reference optical path) is referred to as a reference arm.

The beam splitter 213 is arranged at one end of the reference optical path, and a reference mirror 214 is arranged at the other end. The reference light formed of components having transmitted through the beam splitter 213 is reflected by the reference mirror 214, and returned to the beam splitter 213.

By a reference mirror driver 214A illustrated in FIG. 4, the reference mirror 214 is moved along the traveling direction of the reference light. Thereby, the length of the reference optical path is changed. The reference mirror driver 214A functions to relatively change the length of the measurement optical path and the length of the reference optical path to thereby change the depth position where the intensity of interference between the measurement light and the reference light becomes maximum. Such an operation of changing the interference depth is an example of the operation of changing the focus position of the measurement light.

In this embodiment, a configuration is employed in which the length of the reference optical path is changed, instead of or in addition to this configuration, there may be provided a configuration to change the length of the measurement optical path. The length of the measurement optical path can be changed by, for example, a corner cube that reflects incident measurement light in a direction opposite to the incident direction and a mechanism for moving the corner cube in the incident direction and the reflection direction.

The measurement light formed of components reflected by the beam splitter 213 is deflected by a fixed mirror 215 arranged to be inclined with respect to the measurement optical path, and is directed to a scanner 216. The scanner 216 is, for example, a two-axis optical scanner. This means that the scanner 216 is configured to be capable of two-dimensionally deflecting the measurement light. The scanner 216 is, for example, a mirror scanner including two mirrors which can be deflected in directions perpendicular to each other. The mirror scanner is configured as, for example, a micro-electro-mechanical systems (MEMS). As another example, the scanner 216 may be formed by using one mirror scanner and a rotary prism.

The measurement light output from the scanner 216 is two-dimensionally deflected collimated light. This measurement light is focused by the relay lens 217, and aerially forms an image in a plane (fundus conjugate plane) Pc conjugate to the fundus Ef. Further, the measurement light is once again focused by an objective lens 219 having the function of a focusing lens, and is incident on the subject's eye E. Incidentally, an optical element (dichroic mirror 218) arranged in the fundus conjugate plane Pc is described later.

The objective lens 219 and a lens barrel 219A are moved along the measurement optical path by a lens barrel driver 219B illustrated in FIG. 4. The objective lens 219 and the lens barrel 219A are moved in the optical axis direction according to the refractive power of the subject's eye E. Thus, the fundus conjugate plane Pc is located in a position conjugate to the fundus Ef. As a result, the measurement light is projected onto the fundus Ef as a spot light. The objective lens 219 (and the lens barrel driver 219B) functions as a diopter correction unit that performs correction in accordance with the diopter of the eye E, and also a focus position changing unit that changes a focus position of the measurement light.

Described blow is another example of the diopter correction unit. For example, to deal with the subject's eye with an extreme refractive power like high myopia, a diopter correction lens can be arranged in the measurement optical path. For example, there may be a mechanism (not illustrated) to insert/remove the diopter correction lens into/from the measurement optical path. Besides, it is also possible to use an optical element having a variable refractive power like, for example, Alvarez lens. Such an optical element for diopter correction may be located between the subject's eye E and the objective lens 219, for example.

The measurement light irradiated to the fundus Ef is scattered (and reflected) at various depth positions of the fundus Ef. The backscattered light (return light) of the measurement light from the fundus Ef travels the same path in the reverse direction and is guided to the beam splitter 213.

The beam splitter 213 causes the return light of the measurement light to interfere with the reference light having passed through the reference optical path. At this time, components of the return light which have traveled about the same distance as the length of the reference optical path, i.e., only the backscattered light from the range within the coherence length in accordance with the length of the reference optical path, substantially interfere with the reference light. The interference light generated through the beam splitter 213 is guided to a spectroscope 220. The interference light incident on the spectroscope 220 is dispersed (spectrally resolved) by a diffraction grating 221, and projected on a light receiving surface of the CCD image sensor 223 through a lens 222. Although FIG. 4 illustrates a transmissive diffraction grating as the diffraction grating 221, the diffraction grating 221 may be formed using a spectral element of other forms, such as a reflection diffraction grating.

The CCD image sensor 223 is, for example, a line sensor. The CCD image sensor 223 detects spectral components of the dispersed interference light, and converts them to electric charges. The CCD image sensor 223 integrates the electric charges to generate a detection signal, and sends it to the computer 230.

As described above, the dichroic mirror 218 is arranged to be inclined in a position corresponding to the fundus conjugate plane Pc of the measurement optical path. The dichroic mirror 218 is configured to transmit measurement light in the near-infrared band therethrough and reflect light in the visible band.

Arranged in an optical path branched from the measurement optical path through the dichroic mirror 218 are a flat panel display (FPD) 225 and a lens 226. The flat panel display 225 displays information under the control of a controller 240. As an example of the information displayed on the flat panel display 225 may be cited various types of visual targets that are presented to the subject's eye E. Examples of the visual targets include optotypes (Landolt rings and the like) for subjective visual acuity test, a fixation target to help the subject's eye E to be stable, and the like.

The flat panel display 225 is located in a position conjugate to the fundus conjugate plane Pc (i.e., a position conjugate to the fundus Ef) through the lens 226. The flat panel display 225 may be, for example, a liquid crystal display (LCD) or an organic electroluminescence display (OELD).

Visible light output from the flat panel display 225 is reflected to the dichroic mirror 218 through the lens 226. The visible light is incident on the subject's eye E through the objective lens 219, and reaches the fundus Ef. Thereby, an image (e.g., visual target image) based on the visible light is projected onto the fundus Ef.

An optical element such as a half mirror may be provided instead of the dichroic mirror 218. It is also possible to provide a reflection mirror configured to be insertable into/removable from the measurement optical path. If the dichroic mirror 218 or the half mirror is provided, the projection of a visual target can be performed simultaneously with OCT measurement. On the other hand, when the reflection mirror is provided, OCT measurement and the projection of a visual target are performed at different timings.

While this embodiment employs a Michelson interferometer, it is possible to use any type of interferometer, such as a Mach-Zehnder interferometer. Further, in place of the CCD image sensor, it is possible to use a light receiving element of another type such as a complementary metal-oxide semiconductor (CMOS) image sensor.

In this embodiment, the light reflected by the beam splitter 213 is used as the measurement light, and the light having transmitted through it is used as the reference light. Meanwhile, on the contrary, the light reflected by the beam splitter 213 may be used as reference light, and the light having transmitted through it may be used as measurement light. In this case, the arrangement of the measurement arm and the reference arm is reversed from FIG. 3.

There may be provided a member for converting the properties of the measurement light and/or the reference light. For example, an optical attenuator and a polarization adjuster (polarization controller) may be provided in the reference optical path. The optical attenuator adjusts the amount of the reference light under the control of the computer 230. The optical attenuator includes, for example, a neutral density filter and a mechanism for inserting/removing it into/from the reference optical path. The polarization adjuster adjusts the polarization state of the reference light under the control of the computer 230. The polarization adjuster includes, for example, a polarizing plate arranged on the reference optical path, and a mechanism for rotating it. These are used to adjust the interference intensity of the return light of the measurement light and the reference light.

A front image acquisition optical system may be provided to capture a front image of the subject's eye E. The front image is an image of the anterior segment or the fundus Ef. The front image acquisition optical system forms an optical path branched from the measurement optical path, and includes, for example, an illumination optical system and an imaging optical system similar to those of the conventional fundus camera. The illumination optical system irradiates illumination light consisting of (near) infrared light or visible light to the subject's eye E. The imaging optical system detects the illumination light returning from the subject's eye E (reflected light). The imaging optical system includes a zoom lens system. The imaging optical system shares a common focusing lens (the objective lens 219, the diopter correction lens, etc.) with the measurement optical path, and/or includes a focusing lens separately from the measurement optical path. As another example of the front image acquisition optical system may be cited the same optical system as the conventional SLO.

If there is the front image acquisition optical system, it is possible to further provide an alignment optical system as in the conventional fundus camera. The alignment optical system is configured to form an optical path branched from the measurement optical path, and generates a visual target (alignment visual target) to align the optical system of the apparatus with the subject's eye E. The alignment is performed in a direction (referred to as xy direction) along a plane perpendicular to the measurement optical path (the optical axis of the objective lens 219). Although not illustrated, the alignment optical system generates two alignment light fluxes by using a two-hole aperture from light fluxes output from an alignment light source (LED, etc.). The two alignment light fluxes are guided to the measurement optical path via a beam splitter arranged to be inclined with respect to the measurement optical path. Thus, the alignment light fluxes are projected onto the cornea of the subject's eye E. The alignment light fluxes reflected from the cornea are detected by the image sensor of the front image acquisition optical system.

If there is the alignment optical system, automatic alignment can be performed. Specifically, a data processor 260 of the computer 230 analyzes a signal received from the image sensor of the front image acquisition optical system, and specifies the positions of two alignment visual target images. Further, based on the positions of the two alignment visual target images specified, the controller 240 moves the optical unit 210 in the xy direction such that two cornea reflection light beams are projected as being overlapped each other onto a predetermined position (e.g., the center position) on the light receiving surface of the image sensor. Incidentally, a unit driver 210A is provided to move the optical unit 210.

If there is the front image acquisition optical system, it is possible to further provide a focusing optical system as in the conventional fundus camera. The focusing optical system is configured to form an optical path branched from the measurement optical path, and generates a visual target (split target) for focusing on the fundus Ef. Although not illustrated, the focusing optical system generates two focusing light fluxes by using a split target plate from light fluxes output from a focusing light source (LED, etc.). The two focusing light fluxes are guided to the measurement optical path via a reflective member arranged to be inclined with respect to the measurement optical path. Thus, the focusing light fluxes are projected onto the fundus Ef. The focusing light fluxes reflected from the fundus are detected by the image sensor of the front image acquisition optical system.

If there is the focusing optical system, automatic focusing can be performed. Specifically, the data processor 260 of the computer 230 analyzes a signal received from the image sensor of the front image acquisition optical system, and specifies the positions of two split visual target images. Further, based on the positions of the two split visual target images specified, the controller 240 controls the focusing lens as well as the movement of the focusing optical system (the movement of the objective lens 219, the insertion/removal of the diopter correction lens, etc.) such that two light fluxes reflected from the fundus are projected on a straight line on the light receiving surface of the image sensor.

If there is the front image acquisition optical system, it is possible to perform automatic tracking. Automatic tracking is a function of moving the optical unit 210 in accordance with the movement of the subject's eye E. To perform automatic tracking, alignment and focusing are performed in advance. The automatic tracking is performed, for example, in the following manner: First, the front image acquisition optical system captures a moving image of the subject's eye E. The data processor 260 sequentially analyzes frames of the moving image to monitor the movement (positional change) of the subject's eye E. The controller 240 controls the unit driver 210A to move the optical unit 210 according to the position of the subject's eye E successively acquired. Thereby, the optical unit 210 can follow the movement of the subject's eye E in real time. Thus, it is possible to maintain a suitable positional relationship with proper alignment and focus.

(Control System and Data Processing System)

Described below are the control system and the data processing system of the ophthalmic examination apparatus 200-*a* according to the embodiment. FIG. 4 illustrates an example of the configuration of the control system and the data processing system.

The computer 230 serves as the center of the control system and the data processing system. The computer 230 includes a microprocessor, RAM, ROM, a hard disk drive, a communication interface, and the like. The computer 230 stores computer programs for implementing various types of processing on the ophthalmic examination apparatus 200-*a* in a storage device such as a hard disk drive. The computer 230 may have a dedicated circuit board to perform specific processing. For example, the computer 230 may be provided with a circuit board for implementing processing of forming an OCT image.

(User Interface 280)

The user interface 280 is connected to the computer 230. The user interface 280 includes a display 281 and an operation unit 282. The display 281 includes a display device such as a flat panel display or the like. The operation unit 282 includes buttons, keys, a joystick, an operation device such as an operation panel in the outside and the housing of the ophthalmic examination apparatus 200-*a*. If the computer 230 includes a personal computer, the operation unit 282 may include an operation device of the personal computer (a mouse, a keyboard, a track pad, buttons, etc.).

The display 281 and the operation unit 282 need not necessarily be configured as separate devices, and they may be a device having a display function integrated with an operation function, like a touch panel. In this case, the operation unit 282 includes the touch panel and a computer program. The content of operation performed on the operation unit 282 is input to the controller 240 as an electrical signal. Further, operation or data input may be performed by using a graphical user interface (GUI) displayed on the display 281 and the operation unit 282.

(Controller 240)

The controller 240 is provided to the computer 230. The controller 240 includes a microprocessor, RAM, ROM, a hard disk drive, and the like. The controller 240 includes a main controller 241 and a storage 242.

(Main Controller 241)

The main controller 241 controls each unit in the ophthalmic examination apparatus 200-a. For example, the main controller 241 controls the unit driver 210A, the light source 211, the reference mirror driver 214A, the scanner 216, the lens barrel driver 219B, the CCD (image sensor) 223, the flat panel display 225, the display 281, the data processor 260, and a communication unit 270.

The unit driver 210A has a mechanism for moving the optical unit 210 in a direction (z direction) along the measurement optical path (the optical axis of the objective lens 219) and a direction (xy direction) along a plane perpendicular to the z direction. The reference mirror driver 214A moves the reference mirror 214 along the reference optical path. The lens barrel driver 219B moves the objective lens 219 and the lens barrel 219A along the measurement optical path.

(Storage 242)

The storage 242 stores a variety of data. The storage 242 also stores various types of computer programs and data for operating the ophthalmic examination apparatus 200-a. The data stored in the storage 242 includes data obtained by the ophthalmic examination apparatus 200-a, and data stored in advance. The computer program is designed to operate the ophthalmic examination apparatus 200-a in conjunction with the cloud server 100, for example.

Examples of the data obtained by the ophthalmic examination apparatus 200-a include image data of an OCT image, test data, image data of a front image, and the like. The test data includes data indicating the state of the subject's eye (described in detail later), which is generated by processing the detection result of the interference light obtained by the optical unit 210. The test data may include visual acuity value data obtained by subjective visual acuity test, data generated by processing the image data of a front image, or the like. The storage 242 stores such data as setting information and authorized user authentication information in advance.

(Setting Information)

The setting information indicates the content of the setting of a predetermined item related to the optical unit 210 and the data processor 260. The setting information includes the content of setting related to, for example, at least one of the following items: (1) fixation position; (2) scan pattern; (3) focus position; (4) diopter correction value; (5) and analysis.

(1) The "fixation position" indicates the direction in which the subject's eye E is made to fixate, i.e., a site of the subject's eye E subjected to OCT measurement. Examples of the fixation position include a fixation position for OCT measurement of the macula and its periphery, a fixation position for OCT measurement of the optic disc and its periphery, and a fixation position for OCT measurement of the macula, the optic disc, and their peripheries. A fixation position may be set correspondingly to an arbitrary site of the subject's eye E. The fixation position includes, for example, information indicating the display position of the fixation target (the position of pixels) on the flat panel display 225.

(2) The "scan pattern" indicates a pattern along which the projection position of the measurement light is moved with respect to the subject's eye E. Examples of the scan pattern include one or more line scans (horizontal scan, vertical scan), one or more cross-scans, radial scans, circle scans, and the like. To acquire a three-dimensional image (three-dimensional data set), a three-dimensional scan pattern is employed in which a plurality of scan lines are arranged at sufficiently narrow intervals.

(3) The "focus position" indicates focus conditions applied in OCT measurement. The focus position includes, for example, information indicating the position of the objective lens 219.

(4) The "diopter correction value" indicates conditions used in diopter correction. Specific examples of the diopter correction value include a value indicating the refractive power (visual acuity) of the subject's eye E, use/non-use of a diopter correction lens, a value indicating the refractive power to be applied by the diopter correction lens.

(5) The "analysis" indicates the content of processing performed based on data acquired by the optical unit 210, i.e., the type of test data to be acquired. As with the cloud server 100, examples of the analysis include fundus layer thickness analysis, drusen analysis, optic disc shape analysis, and the like. The fundus layer thickness analysis is a process of obtaining the thickness of a predetermined layer tissue (the retina, sub-tissue of the retina, the choroid, the sclera, etc.) of the fundus. The drusen analysis is a process of obtaining the distribution of drusen (mass of waste products) to be used as a diagnostic material for age-related macular degeneration. The optic disc shape analysis is a process of analyzing a cross-sectional image or a three-dimensional image of the fundus to detect a hole (cut, defect site) in the retina, and thereby determining the shape of the optic disc. In the optic disc shape analysis, a tilt of the optic disc (asymmetry of the shape) can be obtained. These analysis processes are described in detail later.

When OCT measurement is performed for both the left and right eyes of the subject, especially when different settings are used for the left and right eyes, setting information for the left eye (left eye setting information) and setting information for the right eye (right eye setting information) may be provided separately.

Further, when two or more subjects share one of the ophthalmic examination apparatuses 200-a, especially when different settings are used for the subjects, setting information may be provided individually for the subjects. The setting information for each subject is associated with, for example, patient user ID. In this case, for example, setting information is selectively used based on the patient user ID input at the time of test.

Described below is how to create the setting information. The ophthalmic examination apparatus 200-a is rented to the subject, and is used at home or the like of the subject. The setting information is created before the apparatus is rented.

A first example of a method of creating the setting information involves the use of the user interface 280 of the ophthalmic examination apparatus 200-a. For example, on a predetermined setting screen displayed on the display 281, the content of the setting of a predetermined item related to the optical unit 210 and the data processor 260 is entered by using the operation unit 282. The main controller 241 creates the setting information including the content of the setting entered, and stores it in the storage 242. In this case, the user interface 280 functions as an interface.

A second example of a method of creating the setting information involves the use of a computer (e.g., the medical staff terminal 700-f) connected to the ophthalmic examination apparatus 200-a. The medical staff terminal 700-f is a personal computer used by a doctor, for example. The medical staff terminal 700-f is provided with the function (computer program) of creating the setting information. A predetermined setting screen is displayed on the display of the medical staff terminal 700-f. A doctor or the like enters the content of the setting of a predetermined item related to the optical unit 210 and the data processor 260 by using an operation device (keyboard, mouse, etc.). The medical staff terminal 700-*f* sends the entered content of the setting through a cable or the like to the ophthalmic examination apparatus 200-*a*. The ophthalmic examination apparatus 200-*a* receives the content of the setting sent from the medical staff terminal 700-*f* by the communication unit 270. The main controller 241 creates the setting information including the content of the setting received, and stores it in the storage 242. In this case, the communication unit 270 functions as an interface.

The setting information is created with reference to test results and/or test conditions of the subject's eye E, the disease names (types of data to be diagnostic materials), and the like. For example, the fixation position is set with reference to a fixation position used in the past OCT measurement, the disease name, and the like. The scan pattern is set with reference to a scan pattern used in the past OCT measurement, the disease name, and the like. The focus position is set with reference to a focus position used in the past OCT measurement, and the like. The diopter correction value is set with reference to the visual acuity and/or the refractive power obtained in the past test, and the like. The setting of analysis is performed with reference to the types of analysis used in the past test, the disease name, and the like.

Described below are specific examples of the relationship among the test results, the test conditions and/or the disease name, and the contents of the settings. In a macula test, the contents of the settings as follows can be employed:

(1) As the fixation position is used a fixation position where the macula is included in the scan area, for example, a fixation position where the macula is located on the extension line of the optical axis of the measurement optical path.

(2) As the scan pattern, a three-dimensional scan pattern, a radial scan pattern and/or a line scan pattern are/is used.

(3) As the focus position is used a focus position applied in the past OCT measurement, or a focus position obtained by calculation from the measurement value (axial length, refractive power, etc.) of the subject's eye E.

(4) As the diopter correction value is used a diopter correction value applied in the past OCT measurement, or a diopter correction value obtained from the measurement value of the refractive power of the subject's eye E.

(5) As the analysis, the fundus layer thickness analysis (and comparative analysis with the standard layer thickness) is used. In the fundus layer thickness analysis, for example, the thickness of the retina is determined (retinal thickness analysis).

In an optic disc test, the contents of the settings as follows can be employed:

(1) As the fixation position is used a fixation position where the optic disc is included in the scan area, for example, a fixation position where the optic disc is located on the extension line of the optical axis of the measurement optical path.

(2) As the scan pattern, a three-dimensional scan pattern and/or a circle scan pattern are/is used.

(3) As the focus position is used a focus position applied in the past OCT measurement, or a focus position obtained by calculation from the measurement value (axial length, refractive power, etc.) of the subject's eye E.

(4) As the diopter correction value is used a diopter correction value applied in the past OCT measurement, or a diopter correction value obtained from the measurement value of the refractive power of the subject's eye E.

(5) As the analysis, the fundus layer thickness analysis (and comparative analysis with the standard layer thickness) and/or the optic disc shape analysis are/is used. In the fundus layer thickness analysis, for example, the thickness of the retinal nerve fiber layer is obtained (RNFL thickness analysis).

In a glaucoma test, the contents of the settings as follows can be employed:

(1) As the fixation position is used a fixation position where the macula is included in the scan area (e.g., a fixation position where the macula is located on the extension line of the optical axis of the measurement optical path), and/or a fixation position where the optic disc is included in the scan area (e.g., a fixation position where the optic disc is located on the extension line of the optical axis of the measurement optical path).

(2) As the scan pattern, a three-dimensional scan pattern is used.

(3) As the focus position is used a focus position applied in the past OCT measurement, or a focus position obtained by calculation from the measurement value (axial length, refractive power, etc.) of the subject's eye E.

(4) As the diopter correction value is used a diopter correction value applied in the past OCT measurement, or a diopter correction value obtained from the measurement value of the refractive power of the subject's eye E.

(5) As the analysis is used the retinal thickness analysis (and comparative analysis with the standard layer thickness), the RNFL thickness analysis (and comparative analysis with the standard layer thickness), and/or the optic disc shape analysis.

In an age-related macular degeneration test, the contents of the settings as follows can be employed:

(1) As the fixation position is used a fixation position where the macula is included in the scan area, for example, a fixation position where the macula is located on the extension line of the optical axis of the measurement optical path.

(2) As the scan pattern, a three-dimensional scan pattern is used.

(3) As the focus position is used a focus position applied in the past OCT measurement, or a focus position obtained by calculation from the measurement value (axial length, refractive power, etc.) of the subject's eye E.

(4) As the diopter correction value is used a diopter correction value applied in the past OCT measurement, or a diopter correction value obtained from the measurement value of the refractive power of the subject's eye E.

(5) As the analysis, the retinal thickness analysis (and comparative analysis with the standard layer thickness), and/or drusen analysis are/is used.

Part or all of the setting information can be created automatically. In this case, the main controller 241 and/or the medical staff terminal 700-*f* acquire the test results and/or the test conditions of the subject's eye E as well as information about the disease name from the electronic medical records of the subject. Then, the setting information is created to include the information thus acquired.

(Authorized User Authentication Information)

The authorized user authentication information is authentication information for the user (authorized subject) who has been allowed to perform a test by using the ophthalmic examination apparatus 200-*a*. The user authentication information is information used to authenticate a user who is going to perform a test by using the ophthalmic examination apparatus 200-*a*.

Character string information or image information is used as the user authentication information. Examples of the character string information include a patient ID assigned in the medical institution, personal information such as the name of the subject, a character string arbitrarily registered by the subject, a character string set randomly, and the like. Examples of the image information include biometric information (a fingerprint pattern, an iris pattern, a vein pattern, a face-type pattern, etc.), a one-dimensional code, a two-dimensional code, and the like. A voice pattern and a handwriting pattern can also be used as the user authentication information.

The authorized user authentication information is input to the ophthalmic examination apparatus 200-a before the ophthalmic examination apparatus 200-a is lent to the subject, for example. When the authorized user authentication information is a character string, it is input manually using the user interface 280 or the medical staff terminal 700-f, read by using a reader such as a card reader, read from the electronic medical record, or the like. When the authorized user authentication information is image information, it is read by using a reader such as a card reader, input by scanning information written on a paper sheet, read from the electronic medical record or the like, input from a biometric authentication information input device (fingerprint scanner, iris scanner, vein scanner, face analyzer, etc.), or the like. Further, when a voice pattern is employed, the authorized user authentication information is input from a voice input device. If a handwriting pattern is employed, the authorized user authentication information is input from a scanner that has read information written on a paper sheet.

The authorized user authentication information can be stored in the ophthalmic examination apparatus 200-a after the ophthalmic examination apparatus 200-a is installed in the home of the patient. For example, when the ophthalmic examination apparatus 200-a is installed in the home or the like, data communication is established between the ophthalmic examination apparatus 200-a and the cloud server 100. In this process, after the data communication is established, the cloud server 100 can send a patient user ID and authorized user authentication information to the ophthalmic examination apparatus 200-a.

A person, who is going to perform a test using the ophthalmic examination apparatus 200-a, enters user authentication information in a predetermined manner. The entry method corresponds to the type of the user authentication information to be used. That is, the user authentication information is entered on the occasion of using the ophthalmic examination apparatus 200-a in a similar manner to the entry of the authorized user authentication information described above. A constituent element for entering the user authentication information corresponds to a second input unit.

Specific examples of the second input unit include the following:

The user interface 280 for the manual entry of user authentication information;

The communication unit 270 that receives user authentication information entered by using one of the patient terminals 300-b or the like;

A reader such as a card reader to read user authentication information recorded on a recording medium such as a card;

The communication unit 270 that receives user authentication information recorded on an electronic medical record or the like;

A scanner that scans user authentication information written on a paper sheet;

A biometric authentication information input device (fingerprint scanner, iris scanner, vein scanner, face analyzer, etc.) that reads user authentication information consisting of biometric authentication information; and A voice input device for inputting user authentication information consisting of audio information.

When two or more subjects share one of the ophthalmic examination apparatuses 200-a, authorized user authentication information for each of the subjects is stored in the storage 242 in advance.

The cloud server 100 and the ophthalmic examination apparatus 200-a may be configured to be capable of cooperating with each other to test the subject's eye E. For example, the cloud server 100 may be configured to perform personal authentication. In this case, a person who is going to perform a test sends a patient user ID and user authentication information to the cloud server 100 through the ophthalmic examination apparatus 200-a or the patient terminal 300-b. The authentication processor 160 of the cloud server 100 performs authentication based on the patient user ID and the user authentication information received from the ophthalmic examination apparatus 200-a.

When the authentication succeeds, the arithmetic and control unit 110 of the cloud server 100 controls the communication unit 130 to send information indicating permission for the test to the ophthalmic examination apparatus 200-a. In response to the receipt of this permission information, the main controller 241 of the ophthalmic examination apparatus 200-a starts control related to the test.

On the other hand, if the authentication fails, the arithmetic and control unit 110 of the cloud server 100 controls the communication unit 130 to send information indicating prohibition of the test to the ophthalmic examination apparatus 200-a. In response to the receipt of the prohibition information, the main controller 241 of the ophthalmic examination apparatus 200-a stops functions related to the test. Alternatively, in response to the receipt of the prohibition information, the main controller 241 performs control for outputting a message indicating that the authentication has failed or a message prompting the user to enter a patient user ID again (e.g., the main controller 241 controls the display 281 to display a message). If the authentication has failed a predetermined number of times, for example, the arithmetic and control unit 110 of the cloud server 100 may control the communication unit 130 to send information indicating that an authentication error has occurred to one of the patient terminal 300-b, the appointee terminal 400-c, and the medical institution server 600-e.

(Image Forming Unit 250)

The image forming unit 250 generates image data of a two-dimensional cross-sectional image of the subject's eye E based on a detection signal from the CCD image sensor 223. This process includes, as with the conventional spectral-domain OCT, processing such as noise removal (noise reduction), filtering, dispersion compensation, fast Fourier transform (FFT), and the like. If another type of OCT is employed, the image forming unit 250 performs a known process according to the type.

The image forming unit 250 includes, for example, a dedicated circuit board and/or a microprocessor. Incidentally, "image data" and an "image" based on it may be herein identified with each other.

The cloud server 100 can be provided with part or all of the functions of forming an OCT image. If the cloud server 100 has all the functions for forming an OCT image, the ophthalmic examination apparatuses 200-a do not need the image forming unit 250.

When the ophthalmic examination apparatuses 200-a are not provided with the image forming unit 250, the main controller 241 controls the communication unit 270 to send a detection signal (detection data) from the CCD image sensor 223 or data obtained by processing the detection data to the cloud server 100. The test data processor 150 of the cloud server 100 generates image data of a two-dimensional cross-sectional image of the subject's eye E based on the data received from the ophthalmic examination apparatus 200-a.

If both the ophthalmic examination apparatuses 200-a and the cloud server 100 have the image forming function, for example, image data of a two-dimensional cross-sectional image of the subject's eye E can be generated by the cooperation between the image forming unit 250 and the test data processor 150. As another example of processing in this case, when the cloud server 100 has a heavy processing load, the ophthalmic examination apparatus 200-a may perform the image forming process. On the other hand, when having a lower processing load, the cloud server 100 may perform the image forming process. For example, the arithmetic and control unit 110 make the determination on the processing load. The usage conditions of the ophthalmic examination apparatuses 200-a can be taken into account in the determination on the processing load.

(Data Processor 260)

The data processor 260 performs various types of data processing. For example, the data processor 260 performs image processing on an image formed by the image forming unit 250. As an example, the data processor 260 can generate image data of a three-dimensional image of the subject's eye E based on a plurality of two-dimensional cross-sectional images of different cross-sections. The image data of a three-dimensional image is image data in which the positions of pixels are defined by the three-dimensional coordinate system. As one example of the image data of a three-dimensional image may be cited image data formed of three-dimensional arrays of voxels. This image data is referred to as volume data or voxel data. When displaying an image based on volume data, the data processor 260 performs rendering on the volume data (volume rendering and maximum intensity projection (MIP), etc.) to generate image data of a pseudo three-dimensional image viewed from a certain sight line direction. The data processor 260 can image an arbitrary cross-section of a three-dimensional image (multi-planar reconstruction (MPR)).

Further, stack data of a plurality of cross-sectional images may be generated as the image data of a three-dimensional image. The stack data is image data obtained by three-dimensionally arranging a plurality of cross-sectional images acquired along a plurality of scan lines based on the positional relationship between the scan lines. That is, the stack data is image data obtained by representing a plurality of cross-sectional images, which have been originally defined by their respective two-dimensional coordinate systems, by a single three-dimensional coordinate system (i.e., embedding them in one three-dimensional space). The data processor 260 is capable of performing MPR based on the stack data.

The data processor 260 includes, for example, a microprocessor, RAM, ROM, a hard disk drive, a circuit board dedicated for predetermined data processing, and the like. A storage device such as a hard disk drive stores in advance a computer program for the microprocessor to perform data processing described below.

The data processor 260 includes a test data generating unit 261, a stationary determination unit 262, a left/right determination unit 263, an authentication processor 264, and a monitoring processor 265.

(Test Data Generating Unit 261)

The test data generating unit 261 processes the detection result of the interference light obtained by the optical unit 210, and thereby generates test data that indicates the state of the subject's eye E. The test data generating unit 261 is an example of a processor. The test data generating unit 261 processes any of the following as the "detection result of the interference light":

(1) Signal output from the CCD image sensor 223;
(2) Image data generated by the image forming unit 250;
(3) Data obtained in the middle of the process performed by the image forming unit 250 (i.e., data obtained in the middle of the image data forming process); and
(4) Data obtained by processing signals output from the CCD image sensor 223 by a component other than the image forming unit 250.

Described below are examples of processing performed by the test data generating unit 261. As a first example, the test data generating unit 261 can generate layer thickness information of the fundus Ef based on the detection result of the interference light obtained by the optical unit 210. In this case, the test data generating unit 261 functions as a layer thickness information generating unit, and performs the fundus layer thickness analysis (retinal thickness analysis, RNFL thickness analysis, etc.) described above. Further, the test data generating unit 261 may perform the comparative analysis between the layer thickness information obtained by the fundus layer thickness analysis and the standard layer thickness.

The fundus layer thickness analysis is a process for obtaining the thickness (distribution thereof) of a predetermined layer tissue of the fundus Ef based on the detection result of the interference light. The retinal thickness analysis is described as one example thereof. A similar process is performed to determine the thickness of other layer tissues.

In the retinal thickness analysis, for example, a cross-sectional image or a three-dimensional image of the fundus Ef is analyzed to obtain the thickness distribution of the retina in part or all of the scan area. Note that the retinal thickness has different definitions. For example, the retinal thickness may be defined as a thickness from the inner limiting membrane to the inner nuclear layer (photoreceptor inner segment/outer segment (IS/OS) junction), a thickness from the inner limiting membrane to the retinal pigment epithelium, or the like. The retinal thickness obtained by the retinal thickness analysis is defined by one of these definitions.

For example, the retinal thickness analysis is performed in the following manner. First, an OCT image of the fundus Ef is analyzed to specify an image area corresponding to predetermined boundary sites (e.g., the inner limiting membrane and the retinal pigment epithelium). Then, the number of pixels between specified boundary sites is counted to obtain the retinal thickness (distance in the depth direction). For the process of analyzing an OCT image to obtain the thickness of the fundus layer, reference may be had to, for example, Japanese Unexamined Patent Application Publication Nos. 2007-325831, 2008-206684, 2009-61203, and 2009-66015 filed by the present applicant.

The comparative analysis of the retinal thickness is an analysis comparing the retinal thickness obtained by the retinal thickness analysis and normative data stored in advance. The normative data indicates a standard thickness of the retina of the healthy eye. The normative data is created by measuring the retinal thickness of a number of healthy eyes, and obtaining a statistical value of the measurement results (average value, standard deviation, etc.). The comparative analysis determines whether the retinal thickness of the subject's eye E is within the range of that of healthy eyes. Incidentally, when the range of the retinal thickness of eyes with a disease is determined, the comparative analysis may determine whether the retinal thickness obtained by the retinal thickness analysis is within in the range.

The test data generating unit 261 may be configured to be capable of performing the drusen analysis. The drusen analysis is a process of analyzing, for example, an OCT image to obtain the distribution of drusen in part or all of the scan area. The distribution includes the positions and sizes (areas, volumes, diameters) of the drusen in the eye fundus, and the like.

In the drusen analysis, for example, an OCT image is analyzed to specify an image area corresponding to the Bruch's membrane and an image area corresponding to the retinal pigment epithelium. Then, an image area corresponding to a small substantially circular raised shape is specified as drusen (candidates) based on pixel values between these image areas. The process of specifying the image area based on such a shape can be carried out by, for example, image matching with a template of the shape. Further, the test data generating unit 261 obtains the positions, numbers, sizes, and the like of drusen based on the image areas corresponding to the drusen thus specified. Further, evaluation information can be generated for the state of age-related macular degeneration based on the distribution of the drusen acquired.

Incidentally, when there is provided the front image acquisition optical system mentioned above and an image of the fundus Ef can be captured, the drusen analysis can be performed based on the captured image of the fundus Ef. In this drusen analysis, for example, it is determined whether the pixel value of each pixel in the captured image falls within a predetermined range to specify pixels in the range. If the captured image is a color image, drusen are illustrated in a specific color (yellowish white). Accordingly, a range of pixel values corresponding to the specific color is set as the predetermined range in advance. Besides, if the captured image is a monochrome image, drusen are illustrated with characteristic brightness (luminance). Accordingly, a range of pixel values corresponding to the characteristic brightness is set as the predetermined range in advance. Further, an image area corresponding to drusen can be specified by performing template matching based on the standard shape of the drusen (small substantially circular raised shape) or the like.

The optic disc shape analysis may include a process in which a cross-sectional image or a three-dimensional image of the fundus Ef is analyzed to detect a hole (cut, defect site) in the retina to thereby determine the shape of the optic disc. In the optic disc shape analysis, for example, a cross-sectional image or the like is analyzed to specify an image area corresponding to the optic disc and the retinal surface near it. The image area thus specified is analyzed to obtain parameters (optic disc shape parameters) representing the global shape and the local shape (concavity and convexity). Examples of the optic disc shape parameters include the diameter of the cup of the optic disc, the disc diameter, the rim diameter, the depth of the optic disc, and the like.

In addition, the optic disc shape analysis may include a process of obtaining a tilt of the optic disc (asymmetry of the shape). For example, this analysis process is performed in the following manner. First, the test data generating unit 261 analyzes a three-dimensional image obtained by scanning an area including the optic disc to specify the center of the optic disc. Next, the test data generating unit 261 sets a circular area around the center of the optic disc, and divides the circular area radially to obtain a plurality of partial areas. Subsequently, the test data generating unit 261 analyzes a cross-sectional image of the circular area to obtain the height position of a predetermined layer (e.g., the retinal pigment epithelium layer) at each pixel location. Further, the test data generating unit 261 calculates the average value of height positions of the predetermined layer in the partial areas. Next, the test data generating unit 261 compares a pair of average values obtained for a pair of partial areas corresponding to opposite positions with respect to the center of the optic disc to obtain a tilt of the fundus Ef in the opposite directions. The test data generating unit 261 generates tilt distribution information indicating the distribution of the tilt of the fundus Ef in the circular area based on the tilt obtained for a plurality of opposite directions. In addition, evaluation information can be generated for the state of disease based on the tilt distribution information thus generated (and information indicating the standard distribution).

Although the test data described above is based on results of OCT measurement, the test data may include results of other tests. As an example, if the flat panel display 225 can display optotypes (Landolt rings, etc.) for the subjective visual acuity test, the test data generating unit 261 may generate test data that includes results of the subjective visual acuity test.

The subjective visual acuity test is carried out in such a manner that the subject reads the optotypes presented to the subject's eye E. According to a predetermined computer program, the test data generating unit 261 repeats the process of determining whether the response from the subject is correct and the process of determining a visual target to be presented next depending on the determination result. The main controller 241 displays the visual target determined by the test data generating unit 261 on the flat panel display 225. By repeating these processes, the test data generating unit 261 determines the visual acuity value of the subject's eye E, and generates test data including the visual acuity value.

(Stationary Determination Unit 262)

The stationary determination unit 262 determines whether the subject's eye E is substantially stationary based on data acquired by the optical unit 210 (stationary determination). The term "substantially stationary" indicates not only the state where the subject's eye E is stationary, but also the state where the subject's eye E has a level of movement that does not affect OCT measurement. An acceptable range of such movement is arbitrarily set in advance.

Described below are examples of the stationary determination process. As a first example, the stationary determination is made based on the intensity of the return light of the measurement light. The intensity of the return light of the measurement light is maximum when the alignment is correct (because the specular reflection from the cornea is maximum). The intensity of the return light can be obtained by, for example, detecting part of the return light with a photodetector or the like. The stationary determination unit 262 can determine whether the subject's eye E is substantially stationary based on a temporal variation in the intensity of the return light. Besides, the intensity of the interference light is affected by the intensity of the return light. Therefore, the stationary determination unit 262 can make the stationary determination based on a temporal variation in the intensity of a signal from the CCD image sensor 223.

As a second example, when there is provided the front image acquisition optical system mentioned above, the stationary determination can be made in the following manner. First, a moving image of the subject's eye E is captured with the front image acquisition optical system. Thereby, front images (frames) of the subject's eye E are acquired at predetermined intervals. The stationary determination unit 262 is sequentially fed with the front images and analyzes them to detect a characteristic site of the subject's eye E. This characteristic site is, for example, the pupil (or its center) in an anterior segment image, and the optic disc (or its center), the macula (or its center), a blood vessel, or a lesion site in a fundus image. Further, the stationary determination unit 262 monitors changes in the position of the characteristic site in the front images input in time series, and thereby can determine whether the subject's eye E is substantially stationary.

(Left/Right Determination Unit 263)

The left/right determination unit 263 determines whether the subject's eye E is the left eye or the right eye (left-right determination). The left-right determination is made when the test of both the left and right eyes is performed with the ophthalmic examination apparatus 200-*a*, for example. When only one of the left and right eyes is tested, for example, information that indicates the eye to be tested is the left eye or the right eye is stored in the storage 242 in advance.

Even if the test of only one eye is performed, the left-right determination may be made to prevent the fellow eye from being accidentally tested. That is, for example, when the left eye is set as an eye to be tested, if the subject's eye E is determined to be the right eye as a result of the left-right determination, predetermined notification information may be output. This notification information is, for example, display information displayed on the display 281 or the flat panel display 225, or sound information output from an audio output unit (not illustrated). Besides, when the measurement light includes visible components, the notification may be provided by blinking the measurement light, for example.

Described below are examples of the left-right determination. As a first example, the left-right determination is made based on the control state of the unit driver 210A. This example is applied when the position of the optical unit 210 varies depending on whether the left eye or the right eye is tested. As described above, the optical unit 210 is moved by the unit driver 210A under the control of the main controller 241. Every time the main controller 241 controls the unit driver 210A, it sends the control contents to the left/right determination unit 263. The left/right determination unit 263 determines whether the optical unit 210 is placed in a position for the test of the left eye or a position for the test of the right eye based on the control contents received from the main controller 241. Incidentally, a range of the position for the test of the left eye and a range of the position for the test of the right eye are set in advance.

As a second example, when there is provided the front image acquisition optical system mentioned above, the left-right determination can be made by analyzing a front image. If the front image is an image of the anterior eye segment, the inner corner side and the outer corner side can be identified based on, for example, the shape of the eyelid. Thus, it is possible to determine whether the subject's eye E is the left eye or the right eye. If the front image is an image of the fundus, a determination can be made on whether the subject's eye E is the left eye or the right eye based on the position of the optic disc, the position of the macula, the positional relationship between the optic disc and the macular, the distribution of blood vessels, and the like.

As described above, the left/right determination unit 263 has the function of automatically determining whether the subject's eye E is the left eye or the right eye. The determination result is fed to the controller 240. The left/right determination unit 263 functions as a first input unit that feeds the controller 240 with information indicating whether the subject's eye E is the left eye or the right eye. Meanwhile, such an automatic determination function may be dispensed with. For example, the subject (or an assistant) can enter whether the subject's eye E is the left eye or the right eye through the operation unit 282. In this case, the operation unit 282 corresponds to the first input unit.

(Authentication Processor 264)

As described above, the controller 240 receives an input of user authentication information from the second input unit. The controller 240 sends the user authentication information to the authentication processor 264 together with the authorized user authentication information stored in the storage 242. The authentication processor 264 determines whether the user authentication information and the authorized user authentication information match. The authentication processor 264 sends the determination result to the controller 240.

When two or more subjects share one of the ophthalmic examination apparatuses 200-*a*, i.e., when there are two or more authorized subjects, as described above, the authorized user authentication information for each subject is stored in the storage 242. Upon receipt of an input of user authentication information, the controller 240 sends the user authentication information to the authentication processor 264 together with all authorized user authentication information stored in the storage 242. The authentication processor 264 determines whether the user authentication information matches one of pieces of the authorized user authentication information. In other words, the authentication processor 264 searches for authorized user authentication information that matches the user authentication information.

(Monitoring Processor 265)

The monitoring processor 265 monitors the operation state of a predetermined part of the ophthalmic examination apparatus 200-*a*. For example, the monitoring processor 265 detects a malfunction, damage, failure and the like of the predetermined part of the ophthalmic examination apparatus 200-*a*. Alternatively, the monitoring processor 265 detects that there is a risk of a malfunction, damage, failure and the like of the predetermined part of the ophthalmic examination apparatus 200-*a*. As a specific example, the monitoring processor 265 measures the cumulative operation time, and detects that the measured cumulative operation time exceeds a predetermined threshold.

The part of the ophthalmic examination apparatus 200-*a* monitored may include any hardware and/or any software. Examples of the hardware include a microprocessor, RAM, ROM, a hard disk drive, a communication interface, a light source, an optical element, a light receiving element, an actuator, a mechanism, a cable, and the like. Examples of the software include a computer program for apparatus control, a computer program for data processing, and the like.

Described below is an example of a method of monitoring the operation state of the predetermined part. The monitoring processor 265 detects a physical quantity related to monitored hardware. The monitoring processor 265 then determines whether the detection value falls in an acceptable range to thereby determine whether an error occurs in the hardware. Examples of such processing are as follows:

To detect heat and determine whether it is equal to or above a predetermined temperature;

To detect sound emitted by the mechanism, and determine whether it is abnormal according to the frequency thereof or the like; and To detect the displacement of the hardware with an encoder or the like, and determine whether the abnormal operation of the mechanism or rattling is occurring.

As another example of the monitoring method, predetermined data is entered into the microprocessor. It is possible to determine whether the microprocessor is operating correctly or the computer program is normal depending on whether processed data is normal.

The cloud server 100 may be provided with part or all of the functions of the data processor 260 as described above. If the cloud server 100 has all the functions of the data processor 260, the ophthalmic examination apparatuses 200-a do not need the data processor 260.

When the ophthalmic examination apparatus 200-a is not provided with the data processor 260, the main controller 241 controls the communication unit 270 to send, to the cloud server 100, a detection signal (detection data) from the CCD image sensor 223, data obtained by processing the detection data, image data generated by the image forming unit 250, or the like. The test data processor 150 of the cloud server 100 performs predetermined data processing based on the data received from the ophthalmic examination apparatus 200-a.

If both the ophthalmic examination apparatuses 200-a and the cloud server 100 have the data processing function, for example, a predetermined data processing can be performed by the cooperation between the data processor 260 and the test data processor 150. As another example of processing in this case, when the cloud server 100 has a heavy processing load, the ophthalmic examination apparatus 200-a may perform the predetermined data processing. On the other hand, when having a lower processing load, the cloud server 100 may perform the predetermined data processing. For example, the arithmetic and control unit 110 make the determination on the processing load. The usage conditions of the ophthalmic examination apparatuses 200-a can be taken into account in the determination on the processing load.

(Communication Unit 270)

The communication unit 270 performs data communication via the communication line N by an arbitrary method. For example, the communication unit 270 includes a communication interface in accordance with the Internet, a communication interface in accordance with LAN, and a communication interface in accordance with near field communication. The data communication may be wireless or wired communication. A partner of the data communication is, for example, the cloud server 100, the patient terminals 300-b, or the like.

Data transmitted and received by the communication unit 270 may be encrypted. In this case, the controller 240 (or the data processor 260) includes an encryption processor that encrypts transmission data, and a decryption processor that decrypts received data.

[Patient Terminals 300-b]

The patient terminals 300-b are computer terminals that are provided for use by patient users. Examples of the patient terminals 300-b include a computer terminal that a patient user owns, a computer terminal lent to a patient user, or a computer terminal that is installed in a predetermined location (e.g. elderly welfare facilities). The patient terminals 300-b may be in a form of a mobile phone, a smart phone, a tablet computer, a laptop computer, a desktop computer, or the like. An application program is installed in each of the patient terminals 300-b for utilizing the service provided by the cloud server 100. This application program includes, for example, a general purpose browser and/or dedicated application software. Function and usage of the patient terminals 300-b are described separately.

[Appointee Terminals 400-c]

The appointee terminals 400-c are computer terminals that are provided for use by those (appointees) allowed to use the service provided by the cloud server 100. The appointees are users other than patient users and users of the diagnostician terminals 500-d. Examples of the appointees include those who related to patients, medical staff other than the users of the diagnostician terminals 500-d or the medical staff terminals 700-f. Note that the health care worker is a generic name of a person engaged in medical practice. Examples of the medical staff include doctors, dentists, nurses, pharmacists, public health nurses, midwives, clinical laboratory technicians, health laboratory technicians, medical radiation technologists, medical X-ray technicians, nutritionists, national registered dietitians, physical therapists, work therapists, orthoptist, emergency medical technicians, medical accounting personnel, and the like.

Examples of the appointee terminals 400-c include a computer terminal that an appointee user owns, a computer terminal lent to an appointee user, or a computer terminal that is installed in a predetermined location (e.g. hospitals, clinics, elderly welfare facilities, etc.). The appointee terminals 400-c may be in a form of a mobile phone, a smart phone, a tablet computer, a laptop computer, a desktop computer, or the like. An application program is installed in each of the appointee terminals 400-c for utilizing the service provided by the cloud server 100. This application program includes, for example, a general purpose browser and/or dedicated application software. Function and usage of the appointee terminals 400-c are described separately.

[Diagnostician Terminals 500-d]

The diagnostician terminals 500-d are computer terminals that are provided for use by physicians who perform the diagnosis of target diseases of the service provided by the cloud server 100 (or those who enters the diagnostic result on a computer, collectively referred to as diagnostician and the like). Examples of the diagnostician terminals 500-d include a computer terminal that a diagnostician owns, a computer terminal lent to a diagnostician, or a computer terminal that is installed in a predetermined location (e.g. hospitals, clinics, health diagnostic centers, medical checkup centers, test car, etc.). The diagnostician terminals 500-d may be in a form of a mobile phone, a smart phone, a tablet computer, a laptop computer, a desktop computer, or the like. An application program is installed in each of the diagnostician terminals 500-d for utilizing the service provided by the cloud server 100. This application program includes, for example, a general purpose browser and/or dedicated application software. Function and usage of the diagnostician terminals 500-d are described separately.

[Medical Institution Servers 600-e]

The medical institution servers 600-e are servers that are installed in medical institutions (hospitals, clinics, etc.) allowed to use the service provided by the cloud server 100. The medical institution servers 600-e provide the service in cooperation with the cloud server 100, and is configured to operate in conjunction with, for example, a hospital information system (including an ordering system, an electronic medical record system, a receipt system, etc.). The medical institution servers 600-*e* provides the service offered by the cloud server 100 to a plurality of clients (the medical staff terminals 700-*f*). An application program is installed in each of the medical institution servers 600-*e* for utilizing the service provided by the cloud server 100. This application program includes, for example, dedicated application software. Function and usage of the medical institution servers 600-*e* are described separately.

[Medical Staff Terminals 700-*f*]

The medical staff terminals 700-*f* are used to utilize the service provided by the cloud server 100 through the medical institution servers 600-*e*. Examples of the medical staff terminals 700-*f* include a computer terminal that medical staff owns, a computer terminals lent to medical staff, or a computer terminal that is installed in a predetermined location (hospitals, clinics, etc.). The medical staff terminal 700-*f* may be in a form of a mobile phone, a smart phone, a tablet computer, a laptop computer, a desktop computer, or the like. An application program is installed in each of the medical staff terminals 700-*f* for utilizing the service provided by the cloud server 100. This application program includes, for example, a general purpose browser and/or dedicated application software. Function and usage of the medical staff terminals 700-*f* are described separately.

[Financial Institution Servers 800-*g*]

The financial institution servers 800-*g* are servers for processing information dealt by banks and credit card companies. The financial institution servers 800-*g* exchange information related to financial institutions (information on accounting, information on the payment of fees, etc.) with the cloud server 100 regarding the service provided by the cloud server 100. An application program is installed in each of the financial institution servers 800-*g* for utilizing the service provided by the cloud server 100. This application program includes, for example, dedicated application software. Function and usage of the financial institution servers 800-*g* are described separately.

[Insurance Provider Servers 900-*h*]

The insurance provider servers 900-*h* are servers for processing information dealt by public insurance agencies and insurance companies. The insurance provider servers 900-*h* exchange information related to insurance providers (information on accounting, information on insurance benefits, etc.) with the cloud server 100 regarding the service provided by the cloud server 100. An application program is installed in each of the insurance provider servers 900-*h* for utilizing the service provided by the cloud server 100. This application program includes, for example, dedicated application software. Function and usage of the insurance provider servers 900-*h* are described separately.

[Forms of Use]

Described below are forms of use of the patient management system 1 of the present embodiment.

[Registration of Patient User~Ophthalmic Test]

Figure 5A:
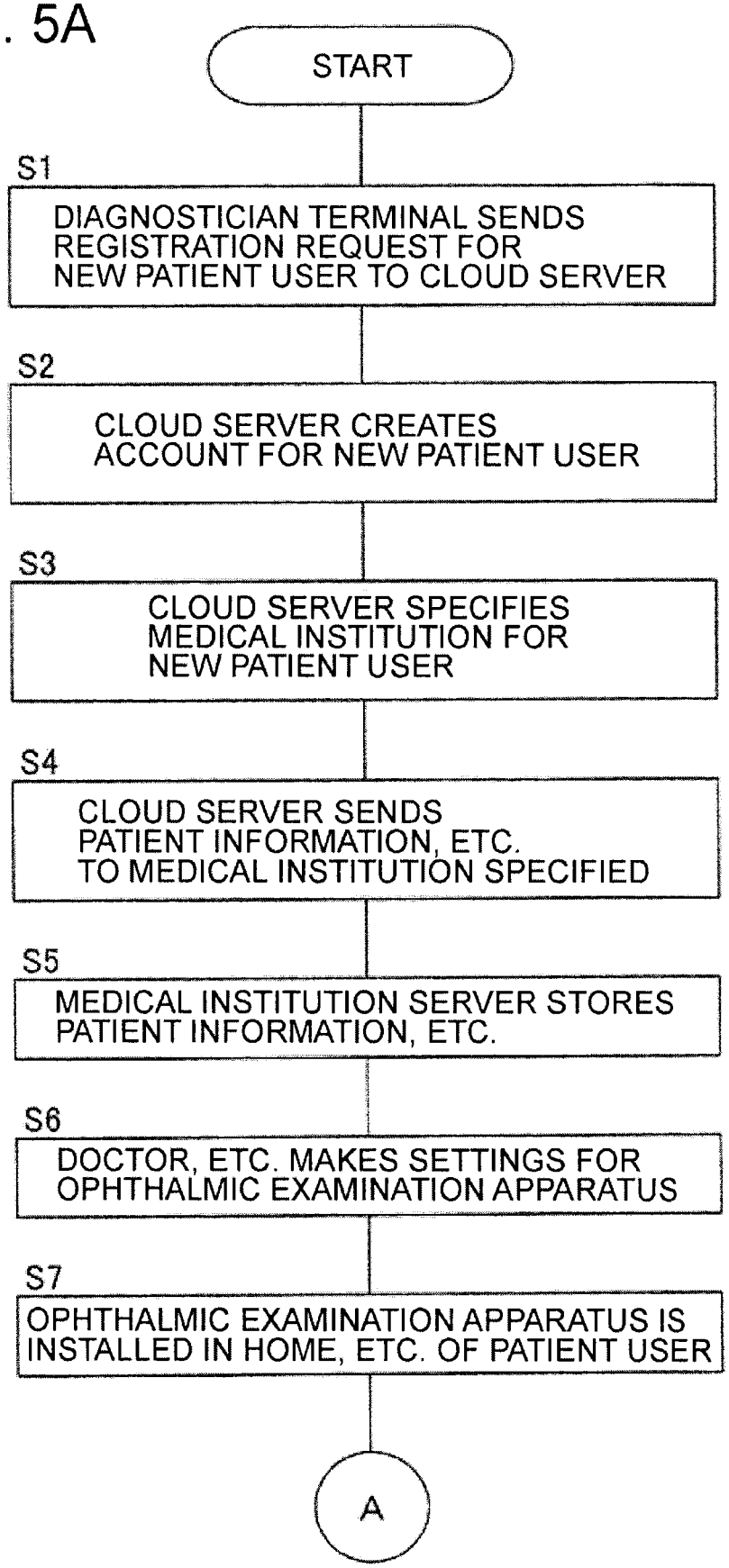
FIG. 5A is a flowchart illustrating an example of the usage of the system of one embodiment.
Figure 5B:
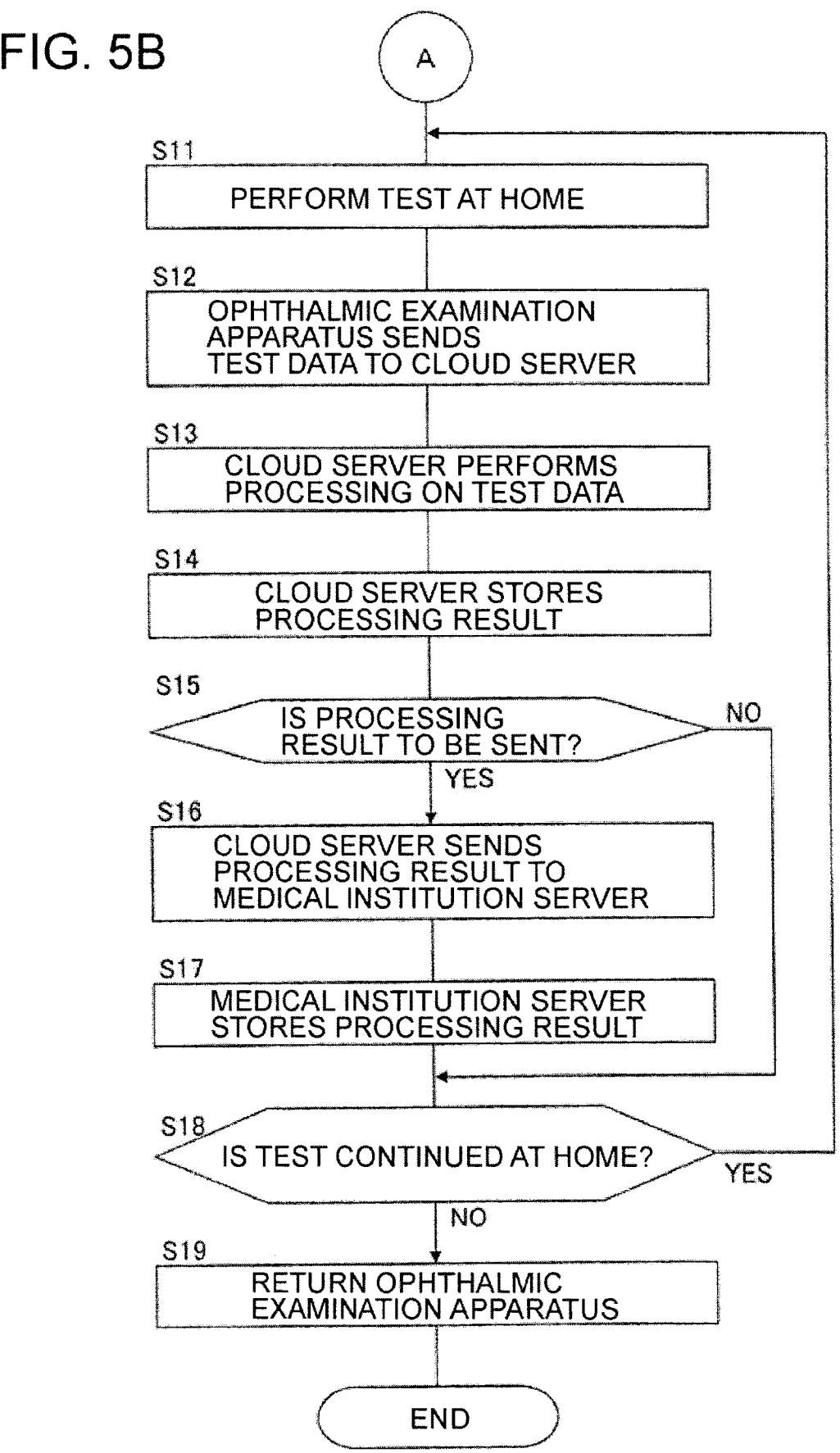
FIG. 5B is a flowchart illustrating an example of the usage of the system of one embodiment.

A description is given of the registration of a patient user, the installation of the ophthalmic examination apparatus 200-*a* in a home or the like, and ophthalmic test at home. FIGS. 5A and 5B illustrate an example of a flow of the processes. FIG. 5A illustrates the process until the ophthalmic examination apparatus 200-*a* is placed in a home or the like of the subject. FIG. 5B illustrates the process from the installation of the ophthalmic examination apparatus 200-*a* to the return of it, especially, the usage of the ophthalmic examination apparatus 200-*a* in the home or the like of the subject.

(S1)

The diagnostician makes a diagnosis for a predetermined disease. The term "predetermined disease" indicates a disease that is the subject of the service provided by the cloud server 100. If a certain examinee is diagnosed as "suffering from a predetermined disease" or "likely to be affected with the disease", the diagnostician or the like requests the cloud server 100 to register the examinee as a new patient user. Specifically, the diagnostician or the like sends information necessary for the new registration, including information about the examinee (name, age, gender, address, insured number, name of disease, etc.), to the cloud server 100 through the diagnostician terminal 500-*d*.

(S2)

The cloud server 100 receives the information sent from the diagnostician terminal 500-*d*. The patient information management unit 141 creates an account for the patient user based on the information received. Incidentally, it may be configured to determine whether the account of the patient user already exists based on the information received. If his/her account already exists, the information received is recorded in the account together with date and time information and the like. On the other hand, if his/her account does not exist, a new account is created.

Although an example is described in which the patient user is introduced through the diagnostician terminal 500-*d*, the patient user may be introduced through any other terminals or servers. For example, a patient user who has already been using the patient management system 1 may introduce an acquaintance as a new patient user by using the patient terminal 300-*b*.

Described below is an example of a case where a server intervenes in the process. The insurance provider server 900-*h* sends information (e.g., name, age, address, contact information, etc.) of insurance users registered in the database of the insurance provider (or insurance users suitable for the service provided by the patient management system 1 from among these registered users) to the cloud server 100. The user information management unit 140 compares the information of the insurance users sent from the insurance provider servers 900-*h* with information recorded in the account of each existing patient user to thereby specify an insurance user who is yet to be registered as a patient user of the service. The arithmetic and control unit 110 sends information (e.g., through e-mail) to prompt the registration to the service to the contact address of the insurance user specified. Incidentally, the cloud server 100 may be configured to request the insurance provider server 900-*h* to send the information prompting the registration to the service to the insurance user. Further, if the cloud server 100 and the insurance provider server 900-*h* share information about existing patient users, or the insurance provider server 900-*h* can access to (part of) information of patient users managed by the cloud server 100, the insurance provider server 900-*h* may perform the process described above as being performed by the cloud server 100.

(S3)

After the account process is completed in step S2, the patient information management unit 141 specifies a medical institution for the patient user. This process is carried out, for example, in the following manner. The patient information management unit 141 determines whether there is a medical institution associated with the patient user. For example, the patient information management unit 141 detects whether information related to medical institution users stored in the storage 120 includes the ID of the patient user (user ID, patient ID, etc.).

If such a medical institution user exists, the patient information management unit 141 determines that the patient user has already been associated with the medical institution user. If the account of the patient user has already been created, the patient information management unit 141 searches for the user ID of the medical institution user that is recorded in this account. Having found the user ID of the medical institution user, the patient information management unit 141 determines that the patient user has already been associated with the medical institution.

Having determined that there is no medical institution user associated with the patient user, the patient information management unit 141 selects a medical institution user for the patient user from among medical institutions managed by the medical institution information management unit 142. In this process, for example, a medical institution user in the location closest to the address of the patient user is selected. In addition, when a plurality of medical institution users have provided examination schedule (booking state of appointments for patients, availability of appointments, etc.), the patient information management unit 141 may select one of the medical institution users which is available for medical care in the shortest period of time, i.e., a medical institution user which can arrange an appointment on the earliest date and time. Besides, any number (one or more) of medical institution users may be selected. The patient information management unit 141 records the user ID of the medical institution thus selected in the account of the patient user.

(S4)

The arithmetic and control unit 110 obtains contact information (IP address) from the account of the medical institution user specified in step S3, and acquires predetermined information (patient information: patient user ID, name, age, gender, address, insured number, name of disease, etc.) from the account of the patient user. Further, the arithmetic and control unit 110 controls the communication unit 130 based on this contact information to send the patient information to the medical institution server 600-*e*.

(S5)

The medical institution server 600-*e* receives the patient information sent from the cloud server 100 in step S4, and stores it in a storage (not illustrated). At this time, an electronic medical record of the patient user may be newly created, or predetermined information may be recorded on an electronic medical record of the patient user that has already been present.

(S6)

At any timing after step S5, settings are made for the ophthalmic examination apparatus 200-*a* to be lent to the patient user. This process is performed by, for example, a doctor or the like in the following manner. Incidentally, the following setting process is performed before the patient user visits the medical institution, at the time of the visit, or after the visit. The settings before the visit can be applied to the case where the diagnostician has performed OCT, and are made by using the settings applied to the OCT. Accordingly, the cloud server 100 is configured to acquire the settings from, for example, the diagnostician terminal 500-*d*. Meanwhile, the settings at the time of or after the visit are made based on settings in OCT that has been carried out by the diagnostician and/or settings in OCT carried out during the visit.

First, an application program for setting is activated. The application program is installed in an apparatus (e.g., the ophthalmic examination apparatus 200-*a*, the medical staff terminal 700-*f*, etc.) used for the setting process. Then, a doctor or the like enters the settings for a predetermined item related to the optical unit 210 and the data processor 260 in the manner described above, for example. The main controller 241 of the ophthalmic examination apparatus 200-*a* creates setting information including the settings entered, for example, in the manner described above. The main controller 241 stores the setting information thus created in the storage 242, for example, in the manner described above. The setting information include, for example, the settings of the fixation position, the settings of the scan pattern, the settings of the focus position, the settings of the diopter correction, the settings of the analysis process, and the like.

The patient information management unit 141 records identification information assigned to the ophthalmic examination apparatus 200-*a* to be lent to the patient user in the account of the patient user.

(S7)

After the completion of the storage of the setting information in step S6, the ophthalmic examination apparatus 200-*a* is transported to the home or the like of the patient user and installed therein. At this time, a fixture or the like can be used for installing the ophthalmic examination apparatus 200-*a* stably. The process from the next step is described referring to FIG. 5B.

(S11)

An ophthalmic test is performed using the ophthalmic examination apparatus 200-*a* installed in the home or the like of the patient user. The ophthalmic test is performed in, for example, the following flow.

First, an instruction is issued to start the test. This instruction may be made by, for example, turning on the power, pressing a test start button, entering user authentication information, or the like.

If the user authentication is performed in the ophthalmic examination apparatus 200-*a*, a patient user ID and user authentication information are entered in the manner described above, for example. The authentication processor 264 determines whether the user authentication information entered matches authorized user authentication information stored in the storage 242 in advance. The authentication processor 264 sends the determination result to the controller 240. If the user authentication information matches the authorized user authentication information, the test is to be performed. On the other hand, if the user authentication information and the authorized user authentication information do not match, the main controller 241 outputs a message prompting the user to enter user authentication information again by voice or by display. The main controller 241 repeats the output of the message until the determination of mismatch reaches a predetermined number of times (e.g., three times). If the determination of mismatch exceeds the predetermined number, the main controller 241 prohibits the test by the ophthalmic examination apparatus 200-*a*. Further, the main controller 241 controls the communication unit 270 to notify the cloud server 100 of the prohibition of the test (that an authentication error has occurred). The doctor or the personnel of the manufacturer recognizes the authentication error through the cloud server 100, and performs predetermined operation for canceling the prohibition of the test (check by phone, etc.). The cloud server 100 or the like may be configured to perform the operation for canceling the prohibition of the test. For example, the cloud server 100 sends information for identity verification to the patient terminal 300-*b* of the patient user. A password is entered based on this information. The cloud server 100 determines whether the person who has entered the password is an authorized patient user based on the validity of the password. If the person is determined to be an authorized patient user, the cloud server 100 sends information for canceling the prohibition of the test to the ophthalmic examination apparatus 200-*a*. The main controller 241 cancels the prohibition of the test based on the information received from the cloud server 100.

Upon receipt of an instruction to start the test, the main controller 241 determines whether this test is the first test after the ophthalmic examination apparatus 200-*a* has been installed in the home or the like of the subject. This process can be implemented by, for example, storing a history (log) in the storage 242 each time a test is performed as well as resetting the test history (test log) prior to the installation of the apparatus. If this test is determined to be a second or subsequent test, subjective visual acuity test is started. On the other hand, if this test is determined to be the first test, the main controller 241 makes settings of relevant part included the optical unit 210 and the data processor 260 based on the setting information stored in the storage 242 in step S6. This process is performed based on, for example, the settings of the fixation position, the settings of the scan pattern, the settings of the focus position, the settings of the diopter correction, the settings of the analysis process, and the like.

Note that in each test performed until the setting information is changed or deleted in step S19, the settings made here are applied.

In this example, OCT measurement and subjective visual acuity test are performed as the test for the subject's eye E. The OCT measurement is performed, for example, in the middle of the subjective visual acuity test. In this case, the main controller 241 first starts the subjective visual acuity test. That is, the first visual target is presented to the subject's eye E based on the optometry program determined in advance.

At this time, the main controller 241 can display the visual target for the subjective visual acuity test at a display position on the flat panel display 225 based on the settings of the fixation position included in the setting information. For example, if the Landolt ring, which is a circle with a break (cutout) in it, is used as the visual target, the Landolt ring can be displayed such that the break is located at a position according to the settings of the fixation position. More generally, the visual target can be displayed on the flat panel display 225 such that a part of the visual target that the subject is particularly interested in is placed at a position according to the settings of the fixation position. Thereby, the visual target for subjective visual acuity test can be assigned a function as a fixation target for performing OCT measurement.

In response to the start of the subjective visual acuity test, the main controller 241 starts the stationary determination process of the subject's eye E. The stationary determination process is performed, for example, in the manner described above, by the stationary determination unit 262. The stationary determination process is being performed until at least it is determined that the subject's eye E is substantially stationary. If it is determined that the subject's eye E is substantially stationary, the OCT measurement is started.

If the subject's eye E cannot be determined to be stationary even after a predetermined time has elapsed from the start of the subjective visual acuity test or even the test has progressed to a predetermined stage, warning can be performed. For example, this warning may be implemented by the main controller 241 that detects the arrival of the warning timing as described above and controls the display 281 or the audio output unit.

In this example, the OCT measurement is performed in the middle of the subjective visual acuity test; however, the tests may be performed at arbitrary timing. For example, OCT measurement may be performed after the completion of the subjective visual acuity test, or the subjective visual acuity test may be performed after the OCT measurement.

In response to that the subject's eye E is determined to be substantially stationary, the main controller 241 controls the optical unit 210 to perform the OCT measurement of the subject's eye E. The OCT measurement is performed based on the settings included in the setting information (e.g., the settings of the fixation position, the settings of the scan pattern, the settings of the focus position, the settings of the diopter correction).

As an example of the operation of the ophthalmic examination apparatus 200-*a*, instead of step S13 (described later), analysis (fundus layer thickness analysis, drusen analysis, optic disc shape analysis, and the like) can be performed based on data acquired by the OCT measurement. This analysis is performed based on the settings of the analysis process included in the setting information.

In the subjective visual acuity test, the visual acuity value of the subject's eye E is determined based on the responses of the subject to visual targets sequentially presented according to the optometry program. The subjective visual acuity test is completed with the determination of the visual acuity.

The test data generating unit 261 generates test data including data obtained by the OCT measurement (e.g., image data, analysis results, etc.) and data obtained by the subjective visual acuity test.

(S12)

The main controller 241 controls the communication unit 270 to send the test data generated by the test data processor 150 to the cloud server 100.

The test data may include supplementary information such as the test date and time, the patient user ID, the identification information of the subject's eye E, the identification information of the ophthalmic examination apparatus 200-*a*, and the like. The test date and time is obtained by the date and time function (system software) installed in the main controller 241, for example. Various types of identification information are stored in the storage 242 in advance.

(S13)

The cloud server 100 receives the test data sent from the ophthalmic examination apparatus 200-*a*. The arithmetic and control unit 110 and/or the test data processor 150 perform(s) predetermined processing on the test data received. As a specific example, the test data processor 150 may apply the fundus layer thickness analysis, the drusen analysis, the optic disc shape analysis, or the like to that data obtained by OCT. Other examples are described later. Incidentally, there is a case where the test data processor 150 does not perform the processing. For example, the ophthalmic examination apparatus 200-*a* may perform the processing, or the test data may be directly used in subsequent processing.

(S14)

The patient information management unit 141 specifies the account of the patient user based on the patient user ID included in the test data, and stores the processing result obtained in step S13 in this account.

(S15)

The arithmetic and control unit 110 determines whether to send the processing result of step S13 to the medical institution server 600-*e*.

As an example of this process, it is possible to determine whether to send the processing result based on whether an abnormality has been found by the analysis (e.g., comparative analysis of the retinal thickness). If an abnormality has been found, it is determined to send the processing result. If an abnormality has not been found, it is determined not to send the processing result.

As another example, the temporal variation of pathological conditions may be obtained with reference to the test data obtained from a plurality of ophthalmic tests, and it may be determined whether the pathological conditions become worse to thereby determine whether to send the processing result based on the determination result. This determination process is performed by, for example, detecting the thickness thinning of the retina (decrease in the retinal thickness) by using threshold processing related to the retinal thickness. When it is determined that the pathological conditions are becoming worse, the processing result is determined to be sent. When it is determined that the pathological conditions are not becoming worse, the processing result is determined not to be sent.

If it is determined to send the processing result (S15: YES), the process proceeds to step S16. If it is determined not to send the processing result (S15: NO), the process proceeds to step S18.

(S16)

If it is determined to send the processing result (S15: YES), the arithmetic and control unit 110 controls the communication unit 130 to send the processing result of step S13 to the medical institution server 600-*e*. This processing result is accompanied by the user ID and the patient ID of the patient user, and the like.

(S17)

The medical institution server 600-*e* receives the processing result and supplementary information sent in step S16. The medical institution server 600-*e* searches for the electronic medical record of the patient user based on the user ID and/or the patient ID included in the supplementary information, and records the processing result on the electronic medical record. Alternatively, the medical institution server 600-*e* stores the processing result in a data storage area created in advance for the patient user.

(S18)

The test described above is repeated until the return of the ophthalmic examination apparatus 200-*a* (S18: YES). The ophthalmic examination apparatus 200-*a* is returned due to, for example, the end of the test (follow-up, etc.) in the home or the like, replacement of the apparatus, maintenance of the apparatus, a change in the setting information, or the like.

(S19)

In response to the determination to return the ophthalmic examination apparatus 200-*a* (S18: NO), the ophthalmic examination apparatus 200-*a* is transported to the medical institution, the manufacturer, or the like. The doctor or the personnel of the manufacturer changes or deletes the setting information stored in the ophthalmic examination apparatus 200-*a*. This is the end of the description of this operation example.

[Instruction to Visit the Medical Institution]

Figure 6A:
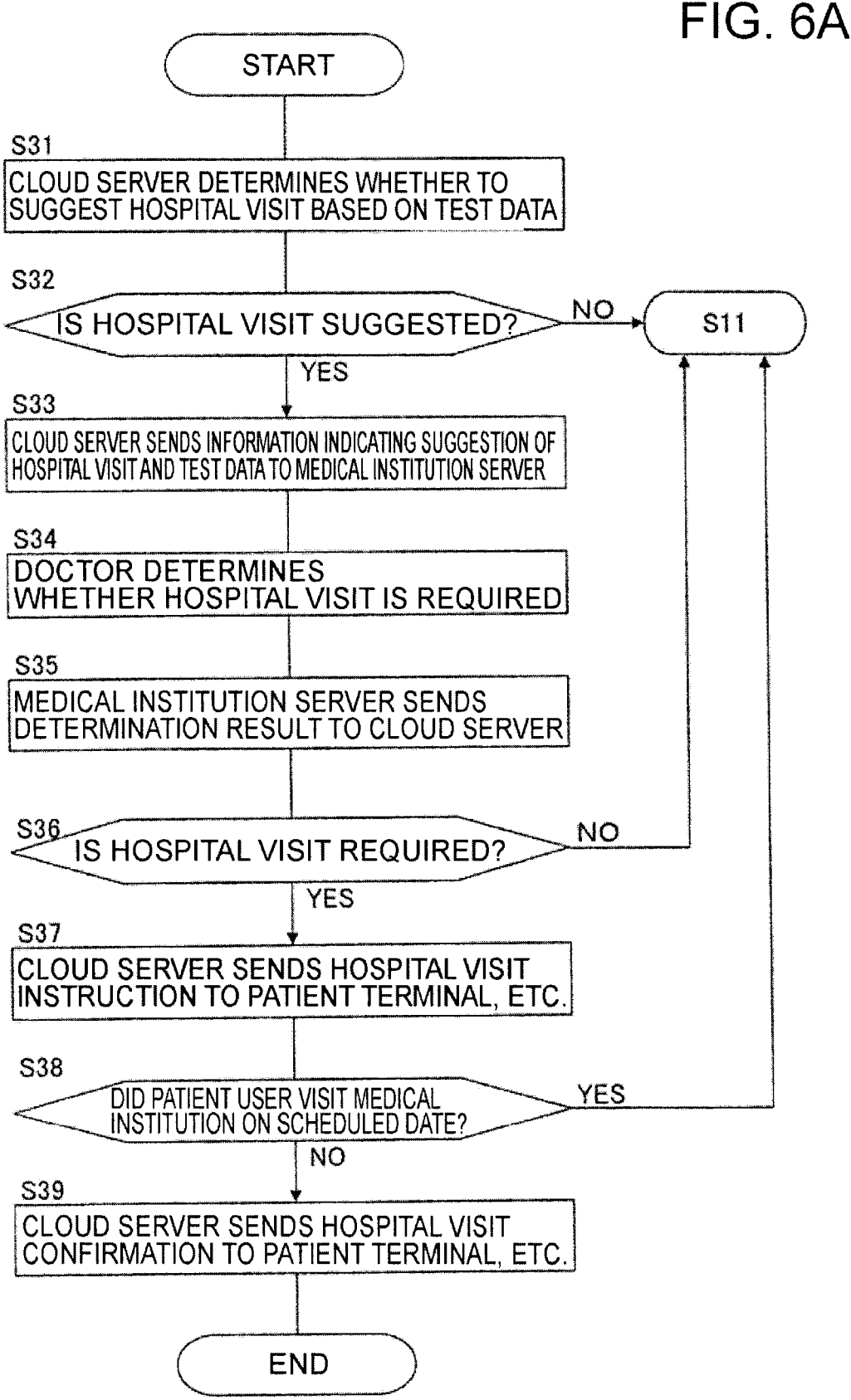
FIG. 6A is a flowchart illustrating an example of the usage of the system of one embodiment.
Figure 6B:
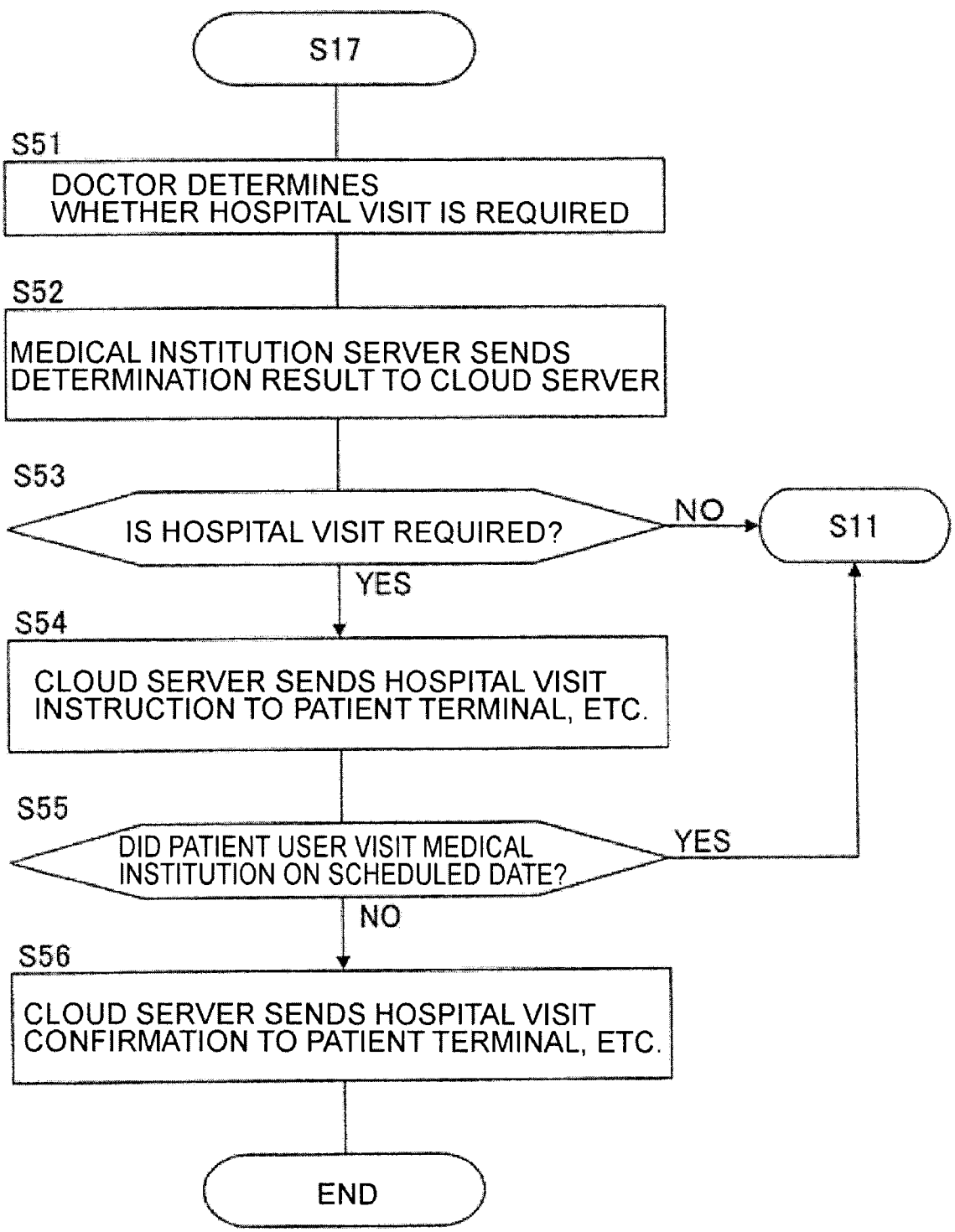
FIG. 6B is a flowchart illustrating an example of the usage of the system of one embodiment.

Two examples are described as to an instruction to the patient user to visit a hospital. The first example explains a case where the cloud server 100 is a starting point (see FIG. 6A). The second example explains a case where the doctor is a starting point (see FIG. 6B).

First Example

FIG. 6A (S31)

As an example of step S13 in FIG. 5B (processing on the test data by the cloud server 100), the arithmetic and control unit 110 determines whether to suggest a hospital visit (hospital attendance) based on the test data of a patient user.

As an example of this process, it is possible to determine whether to suggest a hospital visit based on whether an abnormality has been found by the analysis (e.g., comparative analysis of the retinal thickness). If an abnormality has been found, it is determined to suggest a hospital visit. If an abnormality has not been found, it is determined not to suggest a hospital visit.

As another example, the temporal variation of pathological conditions may be obtained with reference to the test data obtained from a plurality of ophthalmic tests, and it may be determined whether the pathological conditions become worse to thereby determine whether to suggest a hospital visit based on the determination result. This determination process is performed by, for example, detecting the thickness thinning of the retina (decrease in the retinal thickness) by using threshold processing related to the retinal thickness. When it is determined that the pathological conditions are becoming worse, a hospital visit is determined to be suggested. When it is determined that the pathological conditions are not becoming worse, a hospital visit is determined not to be suggested.

(S32)

If it is determined to suggest a hospital visit (S32: YES), the process proceeds to step S33. If it is determined not to suggest a hospital visit (S32: NO), the process proceeds to step S11 in FIG. 5B, and the ophthalmic test is continuously conducted.

(S33)

If it is determined to suggest a hospital visit (S32: YES), the arithmetic and control unit 110 controls the communication unit 130 to send information indicating the suggestion of a hospital visit, and the test data of the patient user (including the test data that is refereed to in the determination process of step S31) together with the user ID and/or the patient ID of the patient user to the medical institution server 600-*e*. Incidentally, if the test data is also stored in the medical institution, the test data need not be sent, and information (e.g., test date and time, test ID, etc.) for identifying the test data may be sent.

(S34)

The medical institution server 600-*e* receives the information sent from the cloud server 100 in step S33. The doctor views the information received by the medical institution server 600-*e* by using the medical staff terminal 700-*f*. The doctor determines whether a hospital visit is required based on the information viewed or the like, and enters the determination result to the medical staff terminal 700-*f*. The medical staff terminal 700-*f* sends the entered determination result to the medical institution server 600-*e*.

(S35)

The medical institution server 600-*e* sends the determination result received from the medical staff terminal 700-*f* to the cloud server 100 together with the user ID of the patient user and the like.

(S36) When it is determined that a hospital visit is not required (S36: NO), the process proceeds to step S11 in FIG. 5B, and the ophthalmic test is continuously conducted. On the other hand, if it is determined a hospital visit is required (S36: YES), the process proceeds to step S37.

(S37)

When it is determined that a hospital visit is required (S36: YES), the arithmetic and control unit 110 controls the communication unit 130 to send information instructing the patient user to visit the medical institution (hospital visit instruction) to the patient terminal 300-*b* of the patient user and/or the appointee terminal 400-*c* of those related to the patient user. The hospital visit instruction may include visit date and time (scheduled visit date and time). In addition, information on a medical institution to be visited (name, address, contact information, etc. of the medical institution) may be provided together with the hospital visit instruction.

(S38)

When the patient user visits the medical institution on the scheduled visit date and time (S38: YES), the process proceeds to step S11 in FIG. 5B, and the ophthalmic test is continuously conducted. Note that the test data and examination results obtained in the medical institution may be sent from the medical institution server 600-*e* to the cloud server 100 to record them in the account of the patient user.

On the other hand, if the patient user does not visit the medical institution on the scheduled visit date and time (S38: NO), the process proceeds to step S39.

(S39)

If the patient user does not visit the medical institution on the scheduled visit date and time (S38: NO), information indicating this is sent from the medical institution server 600-*e* to the cloud server 100. Here, for example, in cooperation with the electronic medical record system, i.e., by detecting that a substantial writing is not made on the electronic medical record of the patient user on the scheduled visit date, the medical institution server 600-*e* can recognize that the patient user has not visited the medical institution. In addition, the doctor may manually enter information indicating that the patient user has not visited the medical institution.

In response to the receipt of the information indicating that the patient user has not visited the medical institution from the medical institution server 600-*e*, the arithmetic and control unit 110 sends information for confirming whether or not the patient user has visited the medical institution (hospital visit confirmation) to the patient terminal 300-*b* of the patient user and/or the appointee terminal 400-*c* of those related to the patient user. The hospital visit confirmation may include visit date and time (scheduled visit date and time) set again. In addition, information on a medical institution to be visited (name, address, contact information, etc. of the medical institution) may be provided together with the hospital visit confirmation. This is the end of the description of this operation example.

Second Example

FIG. 6B (S51)

Described below is an example of processing performed after step S17 in FIG. 5B (storing the processing result of the test data in the medical institution server 600-*e*). The doctor refers to the processing result and the like to determine whether the patient user is in need of a hospital visit, and enters the determination result to the medical staff terminal 700-*f*.

(S52)

The medical staff terminal 700-*f* sends the determination result entered in step S51 to the medical institution server 600-*e*.

(S53)

When it is determined that a hospital visit is not required (S53: NO), the process proceeds to step S11 in FIG. 5B, and the ophthalmic test is continuously conducted. On the other hand, if it is determined a hospital visit is required (S53: YES), the process proceeds to step S54.

(S54)

When it is determined that a hospital visit is required (S53: YES), the arithmetic and control unit 110 controls the communication unit 130 to send information instructing the patient user to visit the medical institution (hospital visit instruction) to the patient terminal 300-*b* of the patient user and/or the appointee terminal 400-*c* of those related to the patient user. The hospital visit instruction may include visit date and time (scheduled visit date and time). In addition, information on a medical institution to be visited (name, address, contact information, etc. of the medical institution) may be provided together with the hospital visit instruction.

(S55)

When the patient user visits the medical institution on the scheduled visit date and time (S55: YES), the process proceeds to step S11 in FIG. 5B, and the ophthalmic test is continuously conducted. Note that the test data and examination results obtained in the medical institution may be sent from the medical institution server 600-*e* to the cloud server 100 to record them in the account of the patient user.

On the other hand, if the patient user does not visit the medical institution on the scheduled visit date and time (S55: NO), the process proceeds to step S56.

(S56)

If the patient user does not visit the medical institution on the scheduled visit date and time (S55: NO), information indicating this is sent from the medical institution server 600-*e* to the cloud server 100. The arithmetic and control unit 110 controls the communication unit 130 to send a hospital visit confirmation to the patient terminal 300-*b* of the patient user and/or the appointee terminal 400-*c* of those related to the patient user. The hospital visit confirmation may include visit date and time (scheduled visit date and time) set again. In addition, information on a medical institution to be visited (name, address, contact information, etc. of the medical institution) may be provided together with the hospital visit confirmation. This is the end of the description of this operation example.

[Notification of Test Results]

Figure 7A:
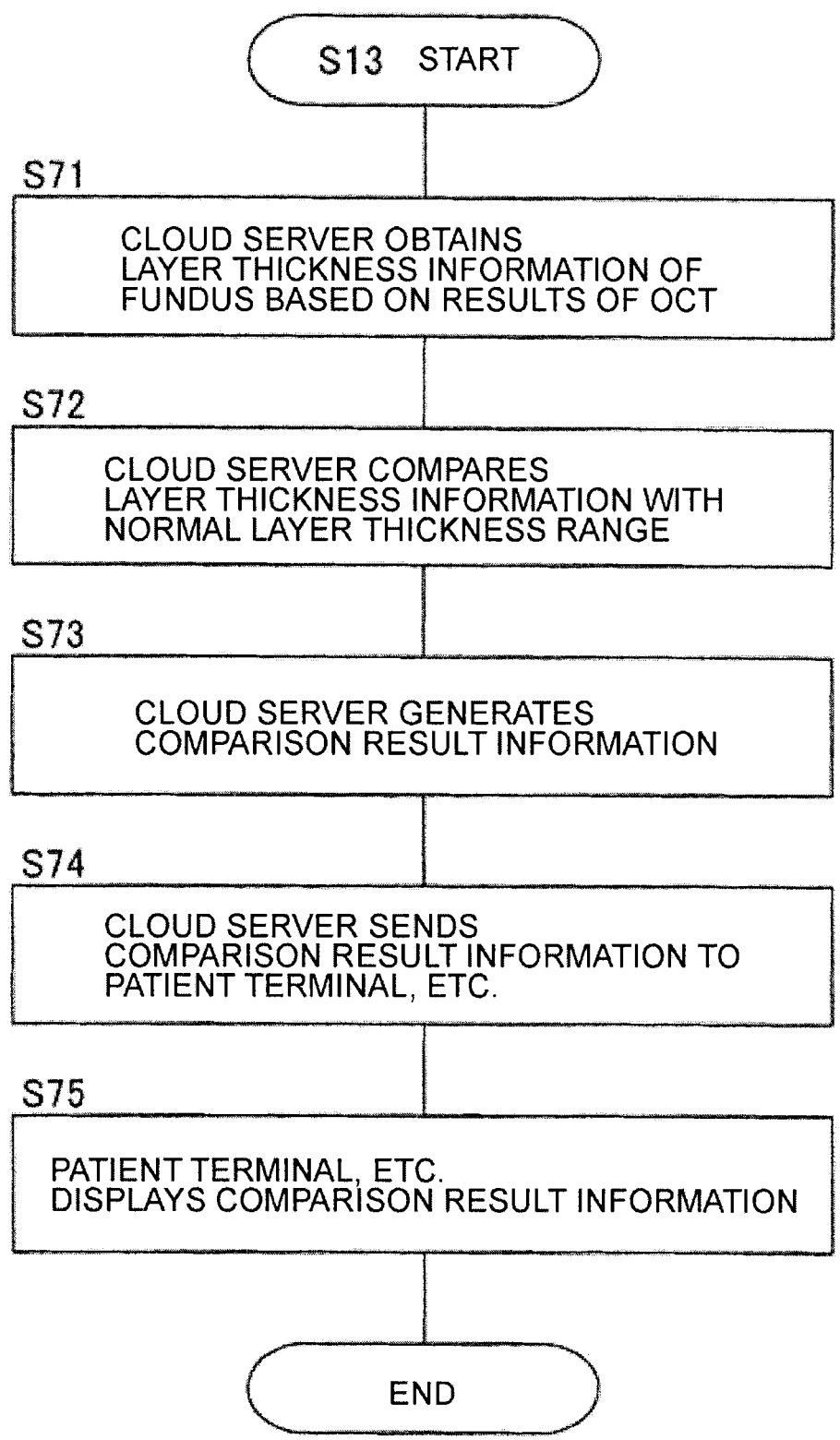
FIG. 7A is a flowchart illustrating an example of the usage of the system of one embodiment.

Two examples are described as to the process of notifying the patient user of test results. The first example explains a case of notifying the patient user of the result of comparing the thickness of the fundus Ef with the normative data (see FIG. 7A). The second example explains a case of notifying the patient user of the temporal variation of the layer thickness of the fundus Ef (see FIG. 7B).

First Example

FIG. 7A (S71)

As an example of step S13 in FIG. 5B (processing on the test data by the cloud server 100), the test data processor 150 performs the fundus layer thickness analysis based on the data obtained by OCT. Thereby, layer thickness information of the fundus Ef can be obtained.

(S72)

Next, the test data processor 150 compares the layer thickness information obtained in step S71 with the normative data indicating the range of the layer thickness of healthy eyes (normal layer thickness range).

(S73)

The test data processor 150 generates information indicating the comparison result (comparison result information) obtained in step S72. The comparison result information may include, for example, information that represents the comparison result by a character string, and/or information that numerically represents the comparison result. Examples of the former include messages such as "an abnormality is not found", "an abnormality is likely to be present", or the like. Examples of the latter include a numerical value indicating the test result (the value of the layer thickness), as well as a numerical value indicating the normal layer thickness range. The numerical value of the normal layer thickness range indicates at least one of the upper and lower limits of the range.

(S74)

The arithmetic and control unit 110 controls the communication unit 130 to send the comparison result information generated in step S73 to the patient terminal 300-b of the patient user and/or the appointee terminal 400-c of those related to the patient user.

(S75)

The patient terminal 300-b and/or the appointee terminal 400-c receive(s) the comparison result information from the cloud server 100, and, for example, display the comparison result information in response to a predetermined operation performed. Thus, the patient user and/or those related to the patient user can check the comparison result information.

Second Example

FIG. 7B (S91)

As an example of step S13 in FIG. 5B (processing on the test data by the cloud server 100), the test data processor 150 performs the fundus layer thickness analysis based on the data obtained by OCT. Thereby, layer thickness information of the fundus Ef can be obtained.

(S92)

The arithmetic and control unit 110 stores the layer thickness information obtained in step S91 in the account of the patient user. Steps S91 and S92 are carried out every time OCT is performed using the ophthalmic examination apparatus 200-a. Through such a process, the layer thickness information obtained in the past is recorded in the account of the patient user together with the test date and time. This means that information on the history of the fundus layer thickness analysis is recorded in the account of the patient user.

(S93)

The test data processor 150 create a graph indicating a change in the layer thickness of the fundus Ef (layer thickness transition graph) based on the history information of the fundus layer thickness analysis recorded in the account of the patient user and the normal layer thickness range (normative data) for the fundus layer thickness analysis. Specific examples of the layer thickness transition graph are described later.

The layer thickness transition graph is created at an arbitrary timing. For example, the layer thickness transition graph may be created each time the fundus layer thickness analysis is performed. Besides, the layer thickness transition graph may be created when an abnormality is found by the fundus layer thickness analysis. In addition, the layer thickness transition graph may be created in response to a request from the patient user or the like.

(S94)

The arithmetic and control unit 110 controls the communication unit 130 to send the layer thickness transition graph created in step S93 to the patient terminal 300-b of the patient user and/or the appointee terminal 400-c of the patient user.

(S95)

The patient terminal 300-b and/or the appointee terminal 400-c receive(s) the layer thickness transition graph from the cloud server 100, and, for example, display the layer thickness transition graph in response to a predetermined operation performed. Thus, the patient user and/or those related to the patient user can check the temporal variation of the layer thickness of the fundus Ef.

FIG. 7C illustrates an example of the layer thickness transition graph. A plurality of layer thickness values T1 to T10 obtained at different timings are recorded in the layer thickness transition graph. The layer thickness values T1 to T10 are based on, for example, OCT measurements made at regular intervals.

The layer thickness transition graph may include information indicating the normal range of the layer thickness (e.g., a character string "Normal" illustrated in FIG. 7C), and/or information to draw the attention of the patient user or the like (e.g., a character string "Warning" illustrated in FIG. 7C). Further, the layer thickness transition graph may include information indicating the time when treatment was performed and content of the treatment. The layer thickness transition graph illustrated in FIG. 7C indicates that drug injections were made on February 5th and May 6th. According to the layer thickness transition graph illustrated in FIG. 7C, in the follow-up observation of the layer thickness of the fundus Ef, it can be seen that an agent is administered by injection immediately after the thinning is detected, and as a result, an improvement is noticed.

[Personal Authentication Using Test Data]

The test data may be used in the personal authentication of the patient user. In this case, image data of the subject's eye, or characteristic information created based on the image data of the subject's eye is recorded in the account of the patient user. Examples of the image data of the subject's eye include image data of a front image of the fundus, image data of a front image of the anterior eye segment, three-dimensional image data (OCT image) of the fundus, three-dimensional image data of the anterior eye segment, and the like. Examples of the characteristic information include information indicating the shape, location, distribution, and the like of a characteristic site extracted from image data. The characteristic site is, for example, a blood vessel, the optic disc, the macula, a lesion site, or the like in the fundus, and the pupil, the iris, a lesion site, or the like in the anterior eye segment.

Figure 8:
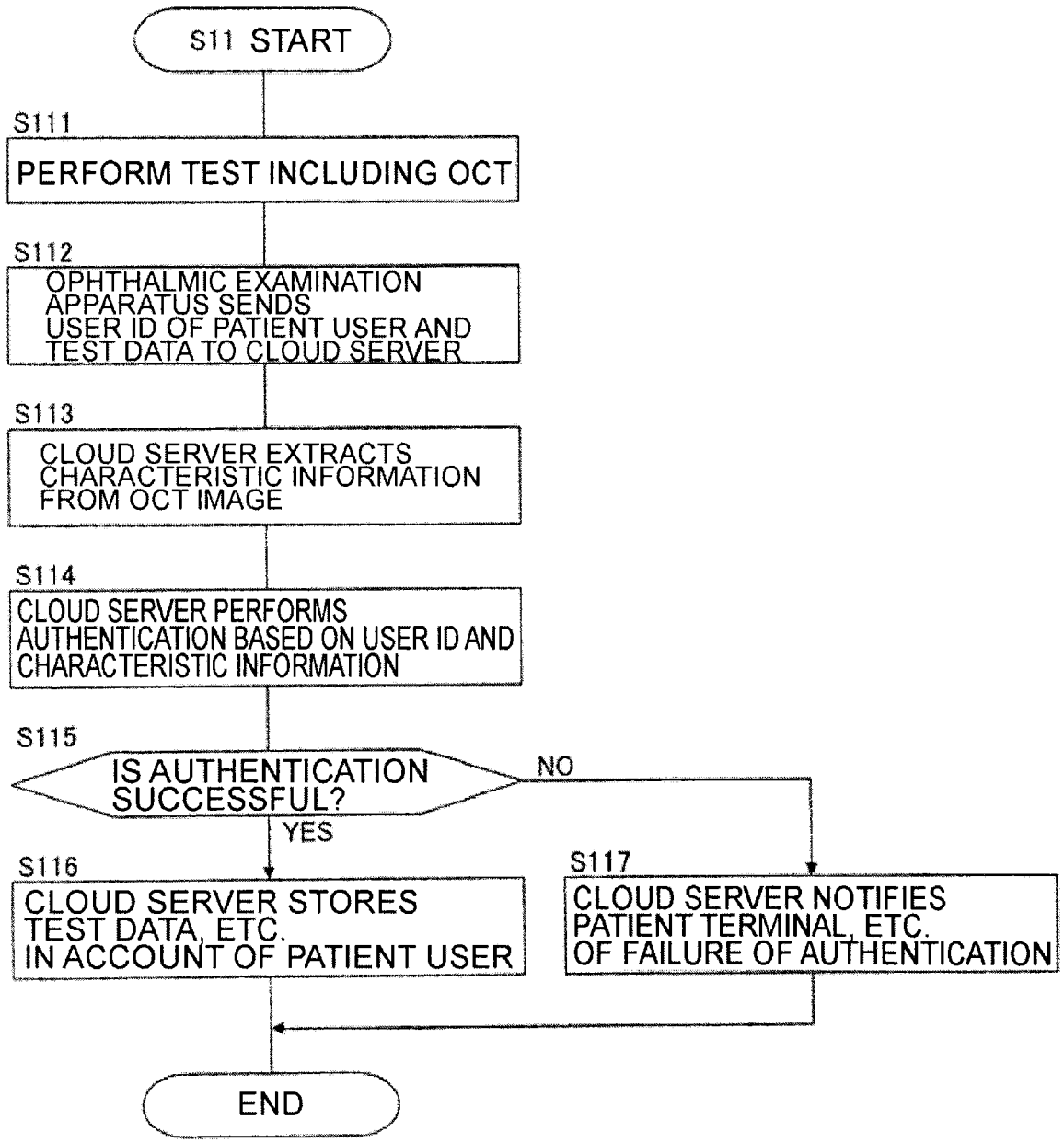
FIG. 8 is a flowchart illustrating an example of the usage of the system of one embodiment.

Although FIG. 8 illustrates an example in which an authentication process is performed based on data obtained by OCT, this is not so limited. Besides, in the example of FIG. 8, the authentication process is performed based on an image of the fundus; however, the target site is not limited to the fundus. As an example, when the ophthalmic examination apparatus 200-a has the front image acquisition optical system, based on front images of the fundus and/or the anterior eye segment obtained by the front image acquisition optical system, the same authentication process as illustrated in FIG. 8 can be performed.

(S111)

In step S11 in FIG. 5B (ophthalmic test in the home or the like), a test of the fundus Ef, including OCT, is performed. In the OCT, for example, three-dimensional scan is applied. Accordingly, a three-dimensional image of the fundus Ef can be obtained.

(S112)

The main controller 241 of the ophthalmic examination apparatus 200-a controls the communication unit 270 to send the user ID of the patient user and the three-dimensional image of the fundus Ef obtained in step S111 to the cloud server 100.

(S113)

The cloud server 100 receives the user ID and the three-dimensional image sent from the ophthalmic examination apparatus 200-a in step S112. The test data processor 150 analyzes the three-dimensional image to extract characteristic information. The characteristic information is, for example, distribution information of blood vessels in a surface layer part of the fundus Ef. The extraction of the characteristic information may include, for example, known image processing such as threshold processing based on the pixel values (brightness values).

(S114)

The arithmetic and control unit 110 specifies the account of the patient user based on the user ID received in step S113, and reads out characteristic information from the specified account to send it to the authentication processor 160. The authentication processor 160 compares the characteristic information read out from the specified account with the characteristic information extracted from the test data in step S113 (three-dimensional image), and determines whether both pieces of the characteristic information substantially match. This comparison process may include, for example, known image processing such as pattern matching and image correlation. The term "substantially match" indicates that both pieces of the characteristic information need not exactly match, but they may be allowed to have some degree of difference. The allowable range of the difference (threshold, etc.) is determined in advance.

(S115 and S116)

When both pieces of the characteristic information substantially match, i.e., if the authentication is successful (S115: YES), the arithmetic and control unit 110 stores the test data and the like (the three-dimensional image, the processing result, etc.) in the account of the patient user.

(S115 and S117)

On the other hand, when both pieces of the characteristic information do not substantially match, i.e., if the authentication fails (S115: NO), the arithmetic and control unit 110 notifies, of the failure of the authentication, the patient terminal 300-b of the patient user and/or the appointee terminal 400-c of those related to the patient user. In this case, the arithmetic and control unit 110 may output such information as prompting to provide a user ID and/or user authentication information again. In this case, the storage 120 stores the user ID of the patient user, the test data, and the like such that the authentication process can be performed again based on the user ID and the user authentication information and the like newly provided.

Described below is another example of the authentication process. In the above authentication process, the test data obtained by the ophthalmic examination apparatus 200-a is compared with the characteristic information (or image data) registered in advance to determine whether a person who has performed a test is an authorized patient user. On the other hand, it can be determined whether the patient user is performing the test appropriately based on the responses in the subjective visual acuity test carried out by using the ophthalmic examination apparatus 200-a. This determination process can also be utilized as a safety check for the patient user.

Such a configuration can be applied to cases, for example, as follows: (1) in a case where the ophthalmic examination apparatus 200-a and the cloud server 100 are connected to be always communicable; (2) in a case where the ophthalmic examination apparatus 200-a and the cloud server 100 start communication in response to a predetermined operation (e.g., power-on, test start instruction, etc.) performed on the ophthalmic examination apparatus 200-a; and (3) in a case where the ophthalmic examination apparatus 200-a and the cloud server 100 start communication in response to the arrival of a predetermined date and time (scheduled test start date and time). If the subjective visual acuity test is not started, the ophthalmic examination apparatus 200-a notifies the cloud server 100 of this. Thus, the cloud server 100 determines that the test of the patient user is not being performed appropriately. When the subjective visual acuity test is started, the ophthalmic examination apparatus 200-a starts presenting visual targets, and sends the contents of the visual targets presented (e.g., the type of the visual targets presented, timing to present the visual targets, etc.) to the cloud server 100. Further, upon receipt of the input of a response to the visual targets presented, the ophthalmic examination apparatus 200-a sends the contents of the response (e.g., whether the response is right or wrong, response timing, etc.) to the cloud server 100. The arithmetic and control unit 110 determines whether the test is being performed appropriately based on the contents of the response received from the ophthalmic examination apparatus 200-a and the test data of subjective visual acuity test performed by the patient user in the past (e.g., last time). This determination process includes, for example, a process of detecting an abnormality in the right or wrong responses, and/or a process of detecting an abnormality in the response timing. In the detection of an abnormality in the right or wrong response, for example, it is detected that the response is incorrect with respect to a visual target for the visual acuity that is lower, by a predetermined value or more, than the visual acuity obtained in the previous test. In the detection of an abnormality in the response timing, for example, it is detected that the elapsed time from the presentation of a visual target to the input of a response is equal to or larger than a predetermined value. These events may result from reasons that, for example, the test is not being performed appropriately, a person other than the patient user is performing the test, condition of the patient user is becoming worse, and the like. If such an event is detected, the arithmetic and control unit 110 performs a predetermined process. Example of the predetermined process include: a process of recording information on the occurrence of an abnormality in the account of the patient user; a process of sending information to the patient terminal 300-b of the patient user; a process of sending information to the appointee terminal 400-c of those related to the patient user; a process of sending information to the appointee terminal 400-c of the family doctor of the patient user; a process of sending information to the medical institution server 600-e; and the like.

[Charging for Paid Services]

The cloud server 100 is capable of providing paid services to the users. The paid services may be provided to any users.

Figure 9:
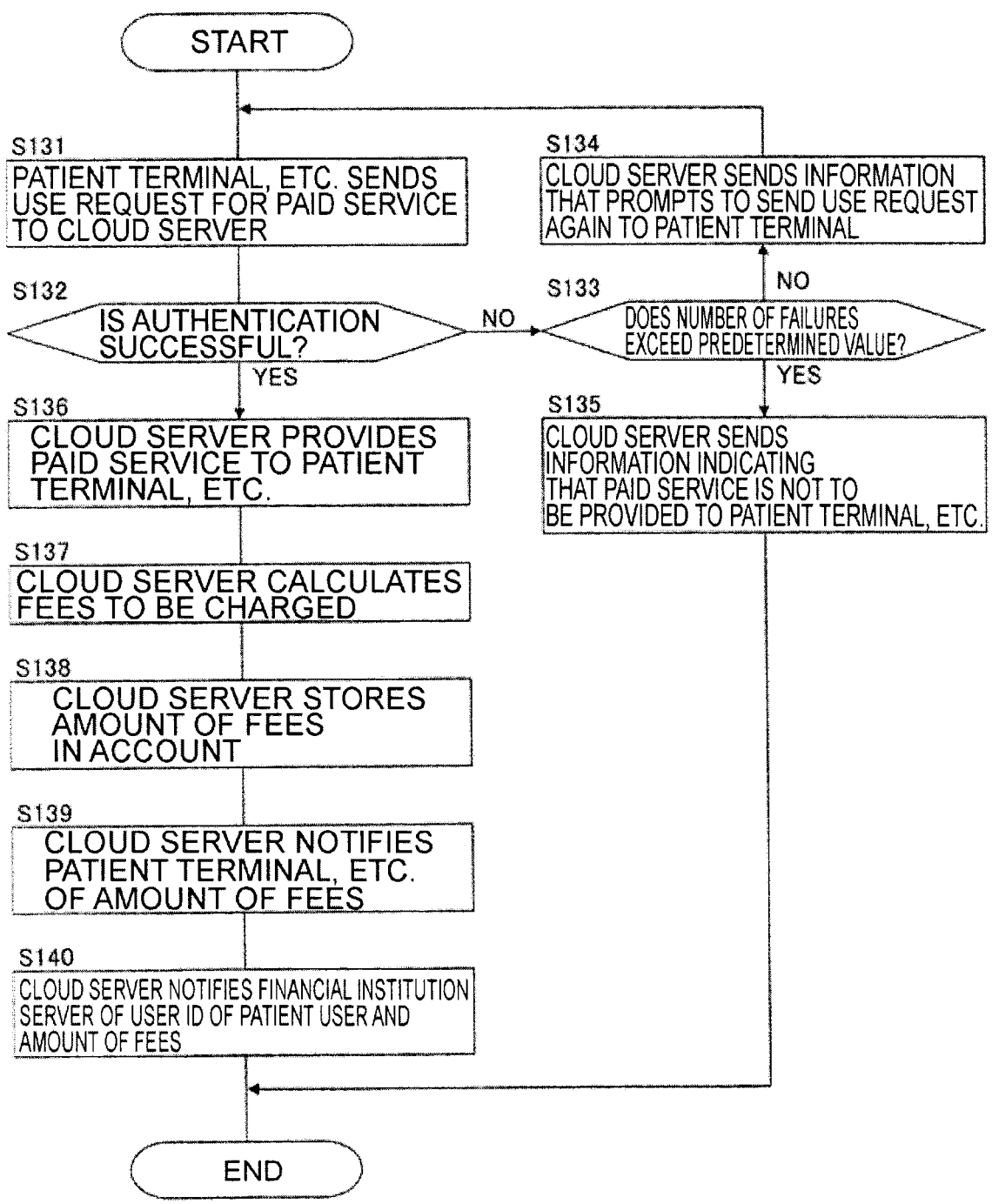
FIG. 9 is a flowchart illustrating an example of the usage of the system of one embodiment.

More specifically, the paid services can be provided to any of patient users, users related to the patients, medical institution users, financial institution users, insurance provider users, and the like. In the following description, an example is described in which a paid service is provided to a patient user (see FIG. 9).

(S131)

The patient user who wishes to use a paid service requests it by operating the patient terminal 300-*b*. Having received the operation, the patient terminal 300-*b* sends a use request for the paid service to the cloud server 100. The use request includes a user ID and user authentication information. Note that the use request for the paid service is made, for example, through a web page provided by the cloud server 100, which can be viewed by means of the patient terminal 300-*b*.

(S132)

The cloud server 100 receives the use request sent from the patient terminal 300-*b* at step S131. The patient information management unit 141 specifies the account of the patient user based on the user ID included in the use request. Further, the authentication processor 160 performs authentication based on the user ID and the user authentication information.

(S133 and S134)

When the authentication fails (S132: NO), the authentication processor 160 determines whether the number of failures exceeds a predetermined value (S133). If the number of failures does not exceed the predetermined value (S133: NO), the arithmetic and control unit 110 controls the communication unit 130 to send, to the patient terminal 300-*b* of the patient user, information that prompts the user to send the use request again (S134). The patient terminal 300-*b* displays the information that prompts the user to send the use request again. The patient user makes the use request again in response to the information displayed (S131).

(S133 and S135)

When the number of authentication failures exceeds the predetermined value (S133: YES), the arithmetic and control unit 110 controls the communication unit 130 to send, to the patient terminal 300-*b* of the patient user, information indicating that the paid service is not to be provided (S135). If the patient user still wishes to use the paid service, he/she contacts the call center or the like of the administrator of the system, and requests for provision of the paid service, reissue of user authentication information, and the like.

(S136)

If the authentication is successful in step S132 (S132: YES), the arithmetic and control unit 110 provides the paid service requested by the patient user through the patient terminal 300-*b* and the like (S136). Examples of paid services are mentioned above.

(S137)

The accounting processor 170 calculates fees to be charged for the paid service provided to the patient user. As described above, the accounting processor 170 refers to the fees for the paid service stored in advance, and determines the amount of fees to be charged to the patient user.

(S138)

The arithmetic and control unit 110 sends the amount of fees calculated in step S137 to the user information management unit 140. The user information management unit 140 records the amount of fees in the account of the patient user. At this time, information related to the service (provision date and time, type, etc.) can be stored with the amount of fees.

(S139)

The arithmetic and control unit 110 notifies the patient terminal 300-*b* of the patient user of the amount of fees calculated in step S137. Incidentally, the cloud server 100 may present the fees for this service on the patient terminal 300-*b* before providing the paid service. In the paid service that charges fees in stages, the amount of fees may be presented on the patient terminal 300-*b* immediately before the occurrence of the next charge.

(S140)

In a step before or after step S139, or in parallel with step S139, the arithmetic and control unit 110 sends the amount of fees calculated in step S137 as well as the user ID and the like of the patient user (account number, credit card number, password, etc.) to the financial institution server 800-*g* of a financial institution that the patient user uses. The financial institution server 800-*g* records the amount of fees in the account and the like of the patient user.

[Other Forms of Use]

Other forms of use of the patient management system 1 are described focusing on differences from the forms of use described above.

A doctor or the like instructs the patient user to carry out a test at a predetermined time interval (e.g. every day, every other day). In the cloud server 100, information that indicates the time interval or a period longer than it (collectively referred to as "predetermined period") is stored in advance in the account of the patient user. The cloud server 100 monitors the interval between tests actually performed in the home or the like. This process is carried out, for example, with reference to the test history (test log) mentioned above. If the test has not been performed for a predetermined period of time, i.e., when test data has not been generated for a predetermined period of time, the arithmetic and control unit 110 of the cloud server 100 performs a predetermined process. Examples of the predetermined process include: a process of recording information indicating that the test has not been performed for a predetermined period of time in the account of the patient user; a process of sending information to the patient terminal 300-*b* of the patient user; a process of sending information to the appointee terminal 400-*c* of those related to the patient user; a process of sending information to the appointee terminal 400-*c* of the family doctor of the patient user; a process of sending information to the medical institution server 600-*e*; and the like.

There is a case where two or more patient users share one of the ophthalmic examination apparatuses 200-*a*. In this case, the storage 242 stores setting information for each subject. Besides, the storage 242 stores authorized user authentication information for each subject. Upon receipt of user authentication information, the main controller 241 searches for authorized user authentication information that matches the user authentication information received, and specifies the setting information corresponding to the authorized user authentication information. The main controller 241 performs setting processing of step S13 based on the setting information specified. The authentication processor 160 of the cloud server 100 also performs similar processing to identify the accounts of the two or more patient users.

[Effects]

Described below are the effects of the patient management system and the patient management server according to the embodiment.

According to the embodiment, the patient management system (1) includes a server (the cloud server 100), a plurality of ophthalmic examination apparatuses (200-*a*), and a plurality of computers (the medical institution servers 600-*e*).

The ophthalmic examination apparatuses (200-a) are assigned to a plurality of patients in advance. The ophthalmic examination apparatus (200-a) are each installed in a home or the like of each of the patients. Each of the ophthalmic examination apparatuses (200-a) can communicate with the server (the cloud server 100) via a communication line (N). The computers (the medical institution servers 600-e) are installed in a plurality of medical institutions. Each of the computers (the medical institution server 600-e) can communicate with the server (the cloud server 100) via a communication line (N).

The ophthalmic examination apparatuses (200-a) each include a first communication unit (the communication unit 270), a test unit (the optical unit 210, the image forming unit 250, the test data generating unit 261, etc.), and a first controller (the controller 240). The first communication unit (the communication unit 270) has a function for communicating with the server (the cloud server 100) via the communication line (N). The test unit (the optical unit 210, etc.) optically tests the eye of a patient allowed to use the ophthalmic examination apparatus (200-a) to thereby generate test data. The first controller (the controller 240) controls the first communication unit (the communication unit 270) to send the test data generated by the test unit to the server (the cloud server 100).

The server (the cloud server 100) includes a second communication unit (the communication unit 130), an information management unit (the user information management unit 140), and a second controller (the arithmetic and control unit 110). The second communication unit (the communication unit 130) has a function for communicating with the ophthalmic examination apparatuses (200-a) and the computers (the medical institution server 600-e) via the communication line (N). The information management unit (the user information management unit 140) is configured to manage the account of each of the patients, in which the test data is stored, and the account of each of the medical institutions. The second controller (the arithmetic and control unit 110) controls the second communication unit (the communication unit 130).

The computers (the medical institution server 600-e) each include a third communication unit, a storage, and a third controller. The third communication unit has a function for communicating with the server (the cloud server 100) via the communication line (N). The third communication unit has, for example, the same configuration as the first communication unit and the second communication unit. The storage stores various types of information. The storage includes, for example, a storage device such as a hard disk drive. When the third communication unit receives information sent from the second communication unit (the communication unit 130), the third controller stores the information in the storage.

With the patient management system, the pathological conditions of a patient can be managed by using the ophthalmic examination apparatus installed in the home of the patient. More specifically, with patient management system of the embodiment, test results obtained by the ophthalmic examination apparatus installed in the home of the patient can be managed individually by the account created for each patient. In addition, test results for a plurality of patients can be centrally managed.

The patient management system (1) of the embodiment may include a plurality of first computer terminals (the diagnostician terminals 500-d). The first computer terminals (the diagnostician terminals 500-d) can communicate with the server (the cloud server 100) via the communication line (N). In this case, the following configuration can be applied. When the second communication unit (the communication unit 130) of the server (the cloud server 100) receives a patient registration request from the first computer terminal (the diagnostician terminals 500-d), the information management unit (the user information management unit 140) creates an account of the patient according to the patient registration request received, and assigns one of the medical institutions to the patient. Further, the second controller (the arithmetic and control unit 110) controls the second communication unit (the communication unit 130) to send information related to the patient to one of the computers (the medical institution server 600-e) installed in the medical institution assigned to the patient.

With this configuration, the process of registering a new patient can be performed automatically. In addition, the process of matching a new patient and a medical institution as well as a process of notifying the new patient of information on the medical institution may also be performed automatically.

The patient management system (1) of the embodiment may be configured to perform the following process when the second communication unit (the communication unit 130) of the server (the cloud server 100) receives the test data from one of the ophthalmic examination apparatuses (200-a). That is, the second controller (the arithmetic and control unit 110) can control the second communication unit (the communication unit 130) to send the test data received to the computer installed in the medical institution assigned to the patient.

With this configuration, a medical institution assigned to the patient can be automatically notified of the test data of a patient obtained by using the ophthalmic examination apparatus (200-a).

In the process of notifying the medical institution of the test data, the second controller (the arithmetic and control unit 110) determines whether to send the test data received from the ophthalmic examination apparatus (200-a) to the computer, and controls the second communication unit (the communication unit 130) to send the test data to the computer only when it has been determined to send the test data.

With this configuration, the medical institution can be notified of the test data obtained by using the ophthalmic examination apparatus (200-a) only when necessary.

The patient management system (1) of the embodiment may be configured as follows. The server (the cloud server 100) may include a test data processor (150). The test data processor (150) performs predetermined processing on the test data received by the second communication unit (the communication unit 130) from one of the ophthalmic examination apparatuses (200-a). Further, the second controller (the arithmetic and control unit 110) controls the second communication unit (the communication unit 130) to send the processing result of the test data obtained by the test data processor (150) to the computer (the medical institution server 600-e) installed in the medical institution assigned to the patient.

With this configuration, after processing is performed on test data of a certain patient acquired by using the ophthalmic examination apparatus (200-a), a medical institution assigned to the patient can be automatically notified of the processing result.

In the process of notifying the medical institution of the processing result of the test data, the second controller (the arithmetic and control unit 110) determines whether to send the processing result of the test data to the medical institution. Only when having determined to send the processing result, the second controller (the arithmetic and control unit 110) controls the second communication unit (the communication unit 130) to send the processing result of the test data to the medical institution.

With this configuration, the medical institution can be notified of the processing result of the test data obtained by using the ophthalmic examination apparatus (200-a) only when necessary.

The patient management system (1) of the embodiment may be configured as follows. When the second communication unit (the communication unit 130) of the server (the cloud server 100) receives test data from one of the ophthalmic examination apparatuses (200-a), the second controller (the arithmetic and control unit 110) determines whether to suggest a hospital visit based on the test data received. If it is determined to suggest a hospital visit, the second controller (the arithmetic and control unit 110) controls the second communication unit (the communication unit 130) to send a suggestion of a hospital visit to a computer (the medical institution server 600-e) installed in the medical institution assigned to the patient.

With this configuration, based on the test data obtained by using the ophthalmic examination apparatus (200-a), it can be suggested for a doctor to assess whether a patient is in need of a hospital visit. Incidentally, taking into account the case where the patient is undergoing home treatment or is in an environment in which home visits are available, the term "hospital visit" is meant to include "home visits". In other words, the "suggestion of a hospital visit" may be the suggestion of medical care, such as the suggestion of home visits.

In the case of suggesting a hospital visit, the following configuration may be applied. The patient management system (1) of the embodiment includes second computer terminals (the patient terminals 300-b, the appointee terminals 400-c) provided for use by a plurality of patients or those related to the patients. The second computer terminals (the patient terminals 300-b, etc.) can communicate with the server (the cloud server 100) via the communication line (N). When the second communication unit (the communication unit 130) receives the determination result as to the necessity of a hospital visit from a computer (the medical institution server 600-e) that has received the suggestion of a hospital visit, the second controller (the arithmetic and control unit 110) can control the second communication unit (the communication unit 130) to send the determination result to one of the second computer terminals (the patient terminals 300-b, etc.) provided for use by the patient or those related to the patient. Note that this process may be performed only when it is determined that the patient is in need of a hospital visit.

With this configuration, a patient and those related to the patient can be automatically notified of the determination result as to the necessity of a hospital visit obtained by a doctor. In particular, if the patient is in need of a hospital visit, the patient and the like may be notified of the fact automatically.

The patient management system (1) of the embodiment may be configured as follows. The patient management system (1) of the embodiment includes second computer terminals (the patient terminals 300-b, the appointee terminals 400-c) provided for use by a plurality of patients or those related to the patients. The second computer terminals (the patient terminals 300-b, etc.) can communicate with the server (the cloud server 100) via the communication line (N). The server (the cloud server 100) includes a test data analyzer (the test data processor 150) configured to analyze the test data received by the second communication unit (the communication unit 130) from one of the ophthalmic examination apparatus (200-a). The second controller (the arithmetic and control unit 110) can control the second communication unit (the communication unit 130) to send the analysis result of the test data obtained by the test data analyzer (the test data processor 150) to the second computer terminal (the patient terminal 300-b, etc.) provided for use by the patient or those related to the patient.

With this configuration, the patient and those related to the patient can be automatically notified of the analyze result of the test data. The patient and the like may be notified of the analysis result created as numerical information or graph information, for example.

The patient management system (1) of the embodiment may be configured as follows. In the account of each of the patients, morphological information that represents the morphology of the patient's eye is stored in advance. The morphological information is, for example, characteristic information created based on an image data of the subject's eye. Examples of the image data of the subject's eye include image data of a front image of the fundus, image data of a front image of the anterior eye segment, three-dimensional image data (OCT image) of the fundus, three-dimensional image data of the anterior eye segment, and the like. Examples of the characteristic information include information indicating the shape, location, distribution, and the like of a characteristic site extracted from the image data. The characteristic site is, for example, a blood vessel, the optic disc, the macula, a lesion, or the like in the fundus, and the pupil, the iris, a lesion, or the like in the anterior eye segment. Further, in this configuration, the test data includes image data that represents the morphology of the eye. Examples of the image data include image data of an OCT image, an image captured of the fundus, or an image captured of the anterior eye segment. The server (the cloud server 100) includes an authentication processor (160). When the second communication unit (the communication unit 130) receives test data from one of the ophthalmic examination apparatuses (200-a), based on the image data included in the test data and morphological information stored in the account of the patient, the authentication processor (160) determines whether the image data represents the morphology of the eye of an authorized patient. When the authentication processor (160) determines that the image data represents the morphology of the eye of the patient, the second controller (the arithmetic and control unit 110) stores the test data in the account of the patient.

With this configuration, the personal authentication of the patient can be performed without an operation for entering authentication information. Moreover, the personal authentication of the patient can be performed without a dedicated device for performing biometric authentication or the like.

The patient management system (1) of the embodiment may be configured as follows. The patient management system (1) of the embodiment includes second computer terminals (the patient terminals 300-b, the appointee terminals 400-c) provided for use by a plurality of patients or those related to the patients. The second computer terminals (the patient terminals 300-b, etc.) can communicate with the server (the cloud server 100) via the communication line (N). The server (the cloud server 100) can provide a predetermined paid service to the second computer terminals (the patient terminals 300-b, etc.). The server (the cloud server 100) includes an accounting processor (170) configured to calculate the amount of fees for the paid service when the paid service has been provided to one of the second computer terminals (the patient terminals 300-*b*, etc.). The second controller (the arithmetic and control unit 110) stores the amount of fees calculated by the accounting processor (170) in the account of the patient. Further, the second controller (the arithmetic and control unit 110) sends information indicating the amount of fees calculated to the second computer terminal (the patient terminal 300-*b*, etc.) provided with the paid service.

With this configuration, charging can be done automatically for the paid service used by the patient.

The patient management system (1) of the embodiment may be configured as follows. The server (the cloud server 100) can provide a predetermined paid service through a plurality of computers (the medical institution servers 600-*e*). The server (the cloud server 100) includes an accounting processor (170) configured to calculate the amount of fees for the paid service when the paid service has been provided through one of the computers (the medical institution servers 600-*e*). The second controller (the arithmetic and control unit 110) stores the amount of fees calculated by the accounting processor (170) in the account of the medical institution. Further, the second controller (the arithmetic and control unit 110) sends information indicating the amount of fees calculated to a computer (the medical institution server 600-*e*) provided with the paid service.

With this configuration, charging can be done automatically for the paid service used by the medical institution (medical staff).

The patient management system (1) of the embodiment may be configured to be capable of performing any process described herein.

According to the embodiment, the patient management server (the cloud server 100) is communicable with a plurality of ophthalmic examination apparatuses (200-*a*) assigned to a plurality of patients, and a plurality of computers (the medical institution servers 600-*e*) installed in a plurality of medical institutions via a communication line (N). The patient management server (the cloud server 100) includes a communication unit (130), an information management unit (the user information management unit 140), and a controller (the arithmetic and control unit 110). The communication unit (130) has a function for communicating with the ophthalmic examination apparatuses (200-*a*) and the computers (the medical institution server 600-*e*) via the communication line (N). The information management unit (the user information management unit 140) is configured to manage the account of each of the patients, and the account of each of the medical institutions. The controller (the arithmetic and control unit 110) controls the communication unit (130). The communication unit (130) receives test data that each of the ophthalmic examination apparatuses (200-*a*) has generated by optically testing the eye of the patient. The information management unit (the user information management unit 140) stores the test data received in the account of the patient. The controller (the arithmetic and control unit 110) controls the communication unit (130) to send the information stored in the account of the patient to a computer (the medical institution server 600-*e*) in one of the medical institutions assigned in advance to the patient.

With this patient management server, the pathological conditions of a patient can be managed by managing test data obtained by the ophthalmic examination apparatus installed in the home of the patient. More specifically, with the patient management server of the embodiment, test results obtained by the ophthalmic examination apparatus installed in the home of the patient can be managed individually by the account created for each patient. In addition, test results for a plurality of patients can be centrally managed.

The patient management server (the cloud server 100) of the embodiment may be configured to be capable of performing any process described herein.

The configurations described above are mere examples for embodying or carrying out the present invention, and therefore susceptible to several modifications and variations (omission, substitution, addition, etc.), all coming within the scope of the invention.

A computer program for realizing the above embodiment may be stored in an arbitrary recording medium that is readable by a computer. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like.

The program may be sent/received through a network such as the Internet or LAN.

The invention claimed is:

1. A patient management system comprising:
   a server;
   a plurality of ophthalmic examination apparatuses, which are communicable with the server via a communication line, and are assigned to a plurality of patients; and
   a plurality of computers, which are communicable with the server via the communication line, and are installed in a plurality of medical institutions;
   wherein each of the ophthalmic examination apparatuses includes a first processor programmed to:
      communicate with the server via the communication line;
      generate test data including image data that represents the morphology of an eye of a patient based on an ophthalmic imaging test of the eye of the patient who is allowed to use the ophthalmic examination apparatus; and
      control sending of the test data to the server,
   the server includes a second processor programmed to:
      communicate with the ophthalmic examination apparatuses and the computers via the communication line;
      manage an account of each of the patients, in which the test data is stored, and an account of each of the medical institutions; and
      control the communication with the ophthalmic examination apparatuses and the computers, and
   each of the computers includes:
      a third processor programmed to communicate with the server via the communication line;
      a memory; and
      the third processor is further programmed to, when the third processor receives information sent from the server, store the information in the memory,
   the patient management system further comprising:
   an appointee computer terminal, which is communicable with the server via the communication line, and which is configured for use by a person related to the patient who is appointed by the patient,
   wherein the second processor in the server is further programmed to analyze the test data received by the server from one of the ophthalmic examination apparatuses, extract characteristic data from the test data, determine if the extracted characteristic data and patient characteristic data stored in advance substantially match each other, and authenticate that the patient is the person for whom the test data was generated, when the determination determines that the extracted characteristic data and the patient characteristic data stored in advance substantially match each other, the second processor in the server is further programmed to send an analysis result of the test data to the person related to the patient, who is appointed by the patient, via the appointee computer terminal, and the server stores the test data in the account of the patient only if the patient is authenticated based on the result of the determination, and the appointee computer terminal is configured to receive a notification to notify the person appointed by the patient of an authentication failure when the authentication of the patient fails.

2. The patient management system according to claim 1, further comprising a first computer terminal, which is communicable with the server via the communication line, wherein, when the second processor of the server receives a patient registration request from the first computer terminal, the second processor creates the account of a patient related to the received patient registration request, and assigns one of the medical institutions to the patient, and the second processor controls sending of information related to the patient to one of the computers installed in the medical institution assigned to the patient.

3. The patient management system according to claim 2, wherein, when the second processor of the server receives the test data from one of the ophthalmic examination apparatuses, the second processor controls sending of the received test data to the computer installed in the medical institution assigned to the patient.

4. The patient management system according to claim 3, wherein the second processor is configured to determine whether to send the received test data to the computer, and control sending of the test data to the computer only when it has been determined to send the test data.

5. The patient management system according to claim 2, wherein the server includes a test data processor configured to perform predetermined processing on the test data received from one of the ophthalmic examination apparatuses, and the second processor is configured to control sending of a processing result of the test data obtained by the test data processor to the computer installed in the medical institution assigned to the patient.

6. The patient management system according to claim 5, wherein the second processor is configured to determine whether to send the processing result to the computer, and control sending of the processing result to the computer only when it has been determined to send the processing result.

7. The patient management system according to claim 2, wherein when the second processor of the server receives the test data from one of the ophthalmic examination apparatuses, the second processor determines whether to suggest a hospital visit based on the received test data, and when it is determined to suggest a hospital visit, the second processor controls sending of a suggestion of a hospital visit to the computer installed in the medical institution assigned to the patient.

8. The patient management system according to claim 7, further comprising a second computer terminal, which is communicable with the server via the communication line, and is provided for use by each of the patient and the person related to the patient, wherein, when the second processor receives a determination result as to necessity of a hospital visit from the computer that has received the suggestion of a hospital visit, and if it has been determined that at least a hospital visit is required, the second processor controls sending of the determination result to the second computer terminal provided for use by the patient and the person related to the patient.

9. The patient management system according to claim 1, wherein in the account of each of the patients, morphological information that represents morphology of the eye of the patient is stored in advance, the server includes an authentication processor configured to, when the second processor receives the test data from one of the ophthalmic examination apparatuses, determine whether the image data represents the morphology of the eye of the patient based on the image data included in the test data and the morphological information stored in the account of the patient, and when the authentication processor determines that the image data represents the morphology of the eye of the patient, the second processor stores the test data in the account of the patient.

10. The patient management system according to claim 1, further comprising a second computer terminal, which is communicable with the server via the communication line, and is provided for use by the patient and the person related to the patient, wherein the server includes an accounting processor configured to calculate fees to be charged for a paid service when the paid service has been provided to the second computer terminal, and the second processor is configured to store the fees calculated by the accounting processor in the account of the patient, and send information indicating the fees to the second computer terminal provided with the paid service.

11. The patient management system according to claim 1, wherein the server includes an accounting processor configured to calculate fees to be charged for a paid service when the paid service has been provided to one of the computers, and the second processor is configured to store the fees calculated by the accounting processor in the account of corresponding one of the medical institutions, and send information indicating the fees to the computer provided with the paid service.

12. The patient management system according to claim 1, wherein the one or more second computer terminals include a patient computer terminal configured for use by the patient.

* * * * *